(12) United States Patent
Chen et al.

(10) Patent No.: US 10,457,659 B2
(45) Date of Patent: Oct. 29, 2019

(54) COMPOSITIONS AND METHODS FOR INCREASING PROLIFERATION OF ADULT SALIVARY STEM CELLS

(75) Inventors: Che-Hong Chen, Fremont, CA (US); Daria Mochly-Rosen, Menlo Park, CA (US); Quynh-Thu Le, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 133 days.

(21) Appl. No.: 14/110,390

(22) PCT Filed: Apr. 26, 2012

(86) PCT No.: PCT/US2012/035119
§ 371 (c)(1),
(2), (4) Date: Mar. 14, 2014

(87) PCT Pub. No.: WO2012/149106
PCT Pub. Date: Nov. 1, 2012

(65) Prior Publication Data
US 2014/0323520 A1 Oct. 30, 2014

Related U.S. Application Data

(60) Provisional application No. 61/480,506, filed on Apr. 29, 2011.

(51) Int. Cl.
| | |
|---|---|
| *A61K 31/437* | (2006.01) |
| *C07D 317/58* | (2006.01) |
| *A61K 31/36* | (2006.01) |
| *C07C 233/29* | (2006.01) |
| *C07C 233/11* | (2006.01) |
| *C07D 215/24* | (2006.01) |
| *C07D 235/16* | (2006.01) |
| *C07D 317/50* | (2006.01) |

(52) U.S. Cl.
CPC ............ *C07D 317/58* (2013.01); *A61K 31/36* (2013.01); *C07C 233/11* (2013.01); *C07C 233/29* (2013.01); *C07D 215/24* (2013.01); *C07D 235/16* (2013.01); *C07D 317/50* (2013.01)

(58) Field of Classification Search
None
See application file for complete search history.

(56) References Cited

U.S. PATENT DOCUMENTS

| | | | |
|---|---|---|---|
| 2,319,808 | A | 5/1943 | Fernholz et al. |
| 4,006,239 | A | 2/1977 | Mayer et al. |
| 4,861,891 | A | 8/1989 | Saccomano et al. |
| 4,957,533 | A | 9/1990 | Arnold et al. |
| 4,992,417 | A | 2/1991 | Katsoyannis |
| 4,992,418 | A | 2/1991 | Katsoyannis |
| 5,004,743 | A | 4/1991 | Young |
| 5,200,534 | A | 4/1993 | Rao |
| 5,202,448 | A | 4/1993 | Carver et al. |
| 5,229,529 | A | 7/1993 | Ueno et al. |
| 5,260,323 | A | 11/1993 | Baader et al. |
| 5,283,253 | A | 2/1994 | Holton et al. |
| 5,294,637 | A | 5/1994 | Chen et al. |
| 5,360,806 | A | 11/1994 | Toki et al. |
| 5,374,605 | A | 12/1994 | Hallenbach et al. |
| 5,409,907 | A | 4/1995 | Blasé et al. |
| 5,415,869 | A | 5/1995 | Straubinger et al. |
| 5,474,978 | A | 12/1995 | Bakaysa et al. |
| 5,504,188 | A | 4/1996 | Baker et al. |
| 5,514,646 | A | 5/1996 | Chance et al. |
| 5,547,929 | A | 9/1996 | Anderson, Jr. et al. |
| 5,650,486 | A | 7/1997 | De Felippis |
| 5,693,609 | A | 12/1997 | Baker et al. |
| 5,700,662 | A | 12/1997 | Chance et al. |
| 5,747,642 | A | 5/1998 | De Felippis |
| 5,922,675 | A | 7/1999 | Baker et al. |
| 5,952,297 | A | 9/1999 | De Felippis et al. |
| 6,034,054 | A | 3/2000 | De Felippis et al. |
| 6,235,791 | B1 | 5/2001 | Breliere et al. |
| 6,384,080 | B1 | 5/2002 | Oku et al. |
| 6,762,176 | B1 | 7/2004 | Lassauniere et al. |

(Continued)

FOREIGN PATENT DOCUMENTS

| | | |
|---|---|---|
| CN | 1749415 A | 3/2006 |
| EP | 1402887 | 3/2004 |

(Continued)

OTHER PUBLICATIONS

ALZET Osmotic Pumps product information: implantation and explantation. Accessed at http://www.alzet.com/products/guide_to_use/implantation_and_explantation.html on Sep. 18, 2016.*
Yu et al. Safrole Induces Apoptosis in Human Oral Cancer HSC-3 Cells. (J. Dent. Res. 90(2), pp. 168-174 (first published online Dec. 20, 2010).*

(Continued)

*Primary Examiner* — Jeffrey S Lundgren
*Assistant Examiner* — Michael J Schmitt
(74) *Attorney, Agent, or Firm* — Bozicevic, Field & Francis LLP; Paula A. Borden; Rudy J. Ng

(57) ABSTRACT

The present disclosure provides methods of increasing proliferation of adult salivary stem cells. The methods include contacting adult salivary stem cells in vivo, in vitro, or ex vivo with an aldehyde dehydrogenase (ALDH) agonist. Increasing proliferation of adult salivary stem cells can be carried out to provide for an increase in the number of adult salivary stem cells in an individual undergoing radiotherapy for head and neck cancer.

8 Claims, 9 Drawing Sheets
Specification includes a Sequence Listing.

(56) References Cited

U.S. PATENT DOCUMENTS

| | | | |
|---|---|---|---|
| 6,780,883 B2 | 8/2004 | Booth et al. | |
| 6,900,338 B1 | 5/2005 | Haj-Yehia | |
| 6,939,882 B1 | 9/2005 | Cooke et al. | |
| 7,179,912 B2 | 2/2007 | Halbrook | |
| 7,569,572 B2 | 8/2009 | Bell et al. | |
| 7,750,025 B2 | 7/2010 | Sanofi-Aventis | |
| 7,790,753 B2 | 9/2010 | Sanofi-Aventis | |
| 7,799,782 B2 | 9/2010 | Munson | |
| 8,124,389 B2 | 2/2012 | Chen et al. | |
| 8,354,435 B2 | 1/2013 | Chen et al. | |
| 8,389,522 B2 | 3/2013 | Mochly-Rosen et al. | |
| 2002/0034783 A1 | 3/2002 | Meyers et al. | |
| 2002/0156281 A1 | 10/2002 | Booth et al. | |
| 2003/0100034 A1 | 5/2003 | Hunter | |
| 2004/0234622 A1 | 9/2004 | Muto et al. | |
| 2004/0242596 A1 | 12/2004 | Kim et al. | |
| 2005/0171043 A1 | 8/2005 | Mochly-Rosen et al. | |
| 2005/0062308 A1 | 9/2005 | Wang et al. | |
| 2005/0215548 A1 | 9/2005 | Wang et al. | |
| 2005/0215645 A1 | 9/2005 | Muto et al. | |
| 2006/0106051 A1 | 5/2006 | Dyckman et al. | |
| 2006/0173050 A1 | 8/2006 | Liu et al. | |
| 2008/0021217 A1 | 1/2008 | Borchardt et al. | |
| 2008/0153926 A1 | 6/2008 | Mochly-Rosen et al. | |
| 2008/0200461 A1 | 8/2008 | Anderson et al. | |
| 2008/0214675 A1 | 9/2008 | Kehler et al. | |
| 2008/0317848 A2 | 12/2008 | Gramatie | |
| 2009/0082431 A1 | 3/2009 | Mochly-Rosen et al. | |
| 2009/0163545 A1 | 6/2009 | Goldfarb | |
| 2009/0203708 A1 | 8/2009 | Churlmin | |
| 2010/0113423 A1* | 5/2010 | Mochly-Rosen | C07C 233/29 514/217.11 |
| 2011/0105602 A2 | 5/2011 | Mochly-Rosen et al. | |
| 2012/0010248 A1 | 1/2012 | Mochly-Rosen et al. | |
| 2012/0101079 A1 | 4/2012 | Kuehnert et al. | |
| 2012/0258947 A1 | 10/2012 | Kuehnert et al. | |
| 2013/0053362 A1 | 2/2013 | Castro et al. | |
| 2013/0253010 A1 | 9/2013 | Chen et al. | |
| 2013/0267501 A1 | 10/2013 | Mochly-Rosen et al. | |
| 2014/0343045 A1 | 11/2014 | Mochly-Rosen et al. | |
| 2015/0105456 A1 | 4/2015 | Mochly-Rosen et al. | |
| 2015/0182511 A1 | 7/2015 | Chen et al. | |

FOREIGN PATENT DOCUMENTS

| | | |
|---|---|---|
| EP | 1402888 | 3/2004 |
| EP | 1438973 A1 | 7/2004 |
| EP | 1477186 A1 | 11/2004 |
| EP | 1661572 A1 | 5/2006 |
| EP | 1862552 | 1/2008 |
| EP | 2018863 | 1/2009 |
| FR | 1581075 | 9/1969 |
| JP | 57122039 | 7/1982 |
| JP | 203351 | 8/1989 |
| JP | 2-115168 | 4/1990 |
| JP | 03184973 A * | 8/1991 |
| JP | 6-321903 | 11/1994 |
| JP | 08208615 | 8/1996 |
| JP | 200526621 | 1/2005 |
| JP | 2012087116 | 5/2012 |
| WO | WO 199710223 | 5/1997 |
| WO | WO1999/23063 | 5/1999 |
| WO | WO1999/32444 | 7/1999 |
| WO | WO1999/54284 | 10/1999 |
| WO | WO 200112604 | 2/2001 |
| WO | WO2001/32928 | 5/2001 |
| WO | WO2002/22599 | 3/2002 |
| WO | WO2002/053544 | 7/2002 |
| WO | WO 2002064568 | 8/2002 |
| WO | WO 2002096135 | 11/2002 |
| WO | WO2003/030937 | 4/2003 |
| WO | WO2003/064391 | 8/2003 |
| WO | 2004005278 | 1/2004 |
| WO | WO2004/022523 | 3/2004 |
| WO | WO2005/014550 | 2/2005 |
| WO | WO2005/057213 | 6/2005 |
| WO | WO2005/07889 | 8/2005 |
| WO | WO 2005084392 | 9/2005 |
| WO | WO 2005011561 | 10/2005 |
| WO | WO2005/110422 | 11/2005 |
| WO | WO 2006091671 | 8/2006 |
| WO | WO 2007034312 | 3/2007 |
| WO | WO 2007075783 | 7/2007 |
| WO | WO2007/110237 | 10/2007 |
| WO | WO 2007136707 A2 | 11/2007 |
| WO | WO2008/002725 | 1/2008 |
| WO | WO 2008014497 | 1/2008 |
| WO | WO2008/024497 | 2/2008 |
| WO | WO 2008021388 | 2/2008 |
| WO | WO 2008082487 | 7/2008 |
| WO | WO 2008082490 A2 | 7/2008 |
| WO | WO2008/112164 | 9/2008 |
| WO | WO2009/146555 | 12/2009 |
| WO | WO2009/156484 | 12/2009 |
| WO | WO 2010028175 A1 | 3/2010 |
| WO | WO 2010062308 A1 | 6/2010 |
| WO | WO 2010137351 A1 | 12/2010 |
| WO | 2011044157 | 4/2011 |
| WO | 2012088420 | 6/2012 |
| WO | WO 2012082862 A2 | 6/2012 |
| WO | WO 2012106534 A2 | 8/2012 |
| WO | 2013006400 | 1/2013 |

OTHER PUBLICATIONS

Borgna et. al."Preparation and Study of the Phytotoxic Activity of N-Aralkyl Subsituted Amides", II Farmaco; Edizione Scientifica, 1977, vol. 32, No. 11, pp. 813-826.

Budas, et. al., "Activation of Aldehyde Dehydrogenase 2 (ALDH2) Confers Cardioprotection in Protein Kinase C Epsilon (PKCε) Knockout Mice", Journal of Molecular and Cellular Cardiology, 2009, vol. 48, pp. 757-764.

Bukhitiarova, et al., "Structure and Anti-inflamitory Activity of Isonicotinic and Nicotine Amides", Pharmaceutical Chemistry Journal, 1997,vol. 31, No. 11, pp. 597-598.

Bukhitiarova, et al., "Possibilities for search for New Analagesics in the series of Arylamides of Isoniotinic and Nocotine Acids", Dopovidi Natsional'Noi Akademii Nauk Ukraini, 1998, No. 8, pp. 162-164.

Chen, et al., CAS:149:548594, 2008.

Chen, et. al., "An Activator of Mutant and Wildtype Aldehyde Dehydrogenase Reduces Ischemic Damage to the Heart" ,Science, 2008, vol. 321, No. 5895, pp. 1493-1495.

Cutshall, et. al., "Nicotinamide N-Oxides as CXCR2 Antagonists", Bioorganic & Medicinal Chemistry Letters, 2001, vol. 11, pp. 1951-1954.

Davis, et. al., "Requirement for Pax6 in Corneal Morphogenesis: a Role in Adhesion", Journal of Cell Science, 2003, vol. 116, No. 11, pp. 2157-2167.

Deng, et al., "Distinct Expression Levels and patterns of Stem Cell Marker, Aldehyde Dehydrogenase Isoform 1 (ALDH1), in Human Epithelial Cancers", PLoS One, 2010, vol. 5, No. 4, pp. 1-11.

Feng, et al., "Isolation and Characterization of Human Salivary Glandsfor Stem Cell Transplantation to Reduce Radiation-Induced Hyposalivation", Radiotherapy and Oncology, 2009, vol. 92, pp. 466-471.

Fernholz, et. al., "Stigmastadienone-22, 23-dibromide and related compounds", 1943, Accession No. 1943: 40468.

Furata et al. "Efficient Synthesis of Phenanthridinone Derivatives via Palladium-Catalyzed Coupling Process", Organic Letters, 2007, vol. 9, No. 2, pp. 183-186.

Gilman et. al. "Organometallic Compounds in the Kolbe and Reimer-Tiemann Reactions", Journal of Organic Chemistry, 1945, Accession No. 1946:2074.

Goldfarb, "Method Using Lifespan-Altering Compounds for Altering the Lifespan of Eukaryotic Organisms, and Screening for Such Compounds", Accession No. 2009:846100.

Grigg, et al. "Synthesis of Cyclopropanes by Intramolecular Attack of N-Nucleophiles on the Central Carbon of (Π-Allyl)Palladium Complexes", Eur. J. Org. Chem. , 2001, vol. 4, pp. 707-712.

(56) References Cited

OTHER PUBLICATIONS

Hess, et al., "Functional Characterization of Highly Purified Human Hematopoietic Repopulating Cells Isolated According to Aldehyde Dehydrogenase Activity", Blood, 2004, vol. 104, No. 6, pp. 1648-1655.
Johnson, et al., "Metabolism, Ecretion, And Pharmacokinetics of (3-{[4-Tert-Butylbenzy)-(Pyridine-3-sulfonyl)-Amino]-Methyl}-Phenoxy)-Acetic Acid, An Ep2recepto-Selective Prostaglandin E2 Agonist, In Male And Femal Sprague-Dawley Rats", 2005, Drug Metabolism and Dispension, vol. 33, No. 8, pp. 1191-1201.
Katritzky, et al., "N-Oxides and Related Compounds. Part X. The Hydrogenation pd some Polyridine 1-oxides", 1958, J. Chem. Soc., pp. 1-18.
Konoplitskaya, et al. "Influence of Cycloprppylethyl-Containing Amines and amides of the Isoenzyme Forms of Rat Liver Aldehyde Dehydrogenase", 1994, vol. 28, No. 1, pp. 7-10.
Larson, et. al. "Disruption of the Coenzyme Binding Site and Dimer Interface Revealed in the Crystal Structure of Mitochondrial Aldehyde Dehydrogenase "Asian" Variant", The Journal of Biological Chemistry Investigation, 2006 vol. 116, No. 2, pp. 506-511.
Li et. al. "Mitochondrial Aldehyde Dehydrogenase-2 (ALDH2) Glu504Lys Polymorphism Contributes to the Variation in Efficacy of Sublingual Nitroglycerin", The Journal of Clinical Investigation, 2006, vol. 116, No. 2, pp. 506-511.
Lombaert, et al., "Rescue of Salivary Gland Function after Stem Cell Transplantation in Irradiated Glands", Plos ONE, 2008, vol. 3, No. 4, pp. 1-13.
Nicoll-Griffith, "Stereoelectronic Model to Explain the Resolution of Enantiomeric Ibuprofen Amides on the Pirkle Chiral Stationary Phase", Journal of Chromatography,1987, vol. 402, pp. 179-187.
Nicoll Griffith's CAS 107 141210, 1987.
Palacios, "Diuretic Action of New Sulfonamide Compounds", 1964, Arch. Inst. Farmacol. Exptl., vol. 16, No. 1, pp. 1-18.
Patani, et. al. "Bioisosterism: A Rational Approach to Drug Design", Chem. Rev., 1996, vol. 96, pp. 3146-3176.
Paruszewski, et al., "Anticonvulsant Activity of Benzylamides of Some Amino Acids and Heterocyclic Acids", Protein and Peptide and Peptide Letters, 2003, vol. 10, No. 5, pp. 475-482.
Perez-Miller, et al., "Alda-1 is an Agonist and Chemical Chaperone for the Common Human Aldehyde Dehydrogenase 2 Variant", Nat Struct Mol Biol, 2010, vol. 17, No. 2, pp. 159-164.
Registry (STN) [online], Apr. 24, 2001 (Searched date: Apr. 25, 2013) CAS Registry No. 332129-81-4.
Registry (STN) [online], Jul. 29, 2001 (Searched date: Apr. 25, 2013), CAS Registry No. 349438-38-6.
Registry (STN) [online], May 14, 2003 (Searched date: Apr. 25, 2013), CAS Registry No. 514816-37-6.
Registry (STN) [online], Aug. 1, 2001 (Searched date:Apr. 25, 2013), CAS Registry No. 349615-88-9.
Registry (STN) [online], Jan. 2, 2001 (searched date:Apr. 25, 2013), CAS Regisrty No. 312526-08-2.
Registry (STN) [online], Jul. 25, 2006 (Searched date: Apr. 25, 2013), CAS Registry No. 895680-72-5.
Registry (STN) [online] Jul. 25, 2006 (Searched date: Apr. 25, 2013), CAS Registry No. 895680-64-5.
Registry (STN) [online], Nov. 5, 2004 (Searched date: Apr. 25, 2013), CAS Registry No. 775317-15-2.
Registry (STN) [online], Jun. 7, 2004 (Searche date: Apr. 25, 2013), CAS Registry No. 690210-80-1.
Registry (STN) [online], Jul. 26, 2001 (Searched date: Apr. 25, 2013), CAS Registry No. 348604-08-0.
Registry (STN) [online], Apr. 2, 2004 (Searched date; Apr. 25, 2013), CAS Registry No. 670271-74-6.
Sato, et. al., "2-Hydroxymethylnicotinic Acid Lactone, 2-Hydroxymethylpyridine-3-acetic Acid Lactone, and Some of their Derivatives", Chem. Pharm. Bull., 1960, vol. 8, No. 5, pp. 427-435.
Satoh, et al. "Comparison of the Inhibitory Action of Synthetic Capsaicin Analogues with Various NADH-ubiquinone Oxidoreductases", Biochimica et Biophysica Acta , 1996, 1273(1) pp. 21-30.

Seto, et. al., "Design and Synthesis of Novel 9-substituted-7-aryl-3,4,5,6-tetrahydro-2H-pyrido [4,3-b]-and [2,3-b]-1,5-oxazocin-6-ones as NK1 Antagonists", 2005, Bioorganic & Medicinal Chemistry Letters, vol. 15, pp. 1479-1484.
Stella et. al. , "Prodrug Strategies to Overcome Poor Water Solubility", Advanced Drug Delivery Reviews, 2007, vol. 59, pp. 677-694.
STN:11/16, 1984, RN 7500-45-0.
Tracey et al. "Product class 4: N-Arylalkanamides, ynamides, enamides, dienamides and allenamides", Science of Synthesis, 2005, Accession No. 2006:359121.
Williams et. al. Foye's Principals of Medicinal Chemistry. 5th edition, 2002, Chapter 2: "Drug Design and Relationship of Functional Groups to Pharmacologic Activity", pp. 59-63.
Zhang, et al. "Automation of Fluorous Solid-Phase Extraction for Parallel Synthesis", J. Comb. Chem. , 2006, vol. 8, pp. 890-896.
U.S. Appl. No. 13/747,106, filed Jan. 22, 2013, Mochly-Rosen, et al.
U.S. Appl. No. 13/717,056, filed Dec. 17, 2012, Mochly-Rosen, et al.
Bohn et al. CAS: 121: 280094 (1994).
Kharchenko et al. CAS: 150: 423065 (2008).
Wu Toxicology 236: 1-6 (2007).
Chen et al. "Interactive effects of lifetime alcohol consumption and alcohol and aldehyde dehydrogenase polymorphisms on esophageal cancer risks," Int J Cancer; 119(12):2827-2831 (2003).
Hashibe et al. "Evidence for an Important Role of Alcohol- and Aldehyde-Metabolizing Genes in Cancers of the Upper Aerodigestive Tract," Cancer Epidemiol Biomarkers Prev.; 15(4):696-703 (2006).
Hashimoto et al. "ALDH2 1510 G/A (Glu487Lys) polymorphism interaction with age in head and neck squamous cell carcinoma," Tumour Biol; 27(6):334-338 (2006).
Himel et al., "Fluorescent analogs of insecticides and synergists. Synthesis and reactions of active-site-directed fluorescent probes," J. Arg. Food Chem 19(6): 1175-1180 (1971).
Huigsen et al., CAS: 46: 45365 (1952).
Moussa et al. CAS: 146: 337551 (2007).
Weintraub et al., CAS: 143405804 (2005).
Yokoyama et al. "Genetic Polymorphisms of Alcohol and Aldehyde Dehydrogenases and Risk for Esophageal and Head and Neck Cancers," Alcohol; 35(3):175-185 (2005).
Zhang et al., "Automation of Fluorous Solid-Phase Extraction for Parallel Synthesis," J. Comb. Chem. 8(6):890-896 (1994).
Chaturvedi, A. K. et. al.,"Effects of choline acetyltransferase inhibitors on the growth and differentiation of mouse neuroblastoma cells in culture", Research Communications in Chemical Pathology and Pharmacology, 37(3), 491-494 (1982).
Chung, W. K. Et. El. "Synthesis and antitumor activities of potential antineoplastic agents. IV. Synthesis and antitumor activities of N-substituted-p-arsanilic acid", Yakhak Hoechi, 1971, 15(1), 16-23 & CAPLUS Accession No. 1974:115993.
Dimmock et al. "Evaluation of some mannich bases derived from substituted acetophenones against p-388 Lymphocyctic leukemia and on respiration in isolated rat liver mitochondria," J. Pharmaceutical Sciences 72(8) 387-894 (1983).
Gul, H. I. El Al. "Evaluation of the cytotoxicity of some mono-Mannich bases and their corresponding azine derivatives against androgen-independent prostate cancer cells", Arzneim.-Forsch./Drug Res., 56(12), 850-855 (2006).
Huang, et al., "Antineoplastic activities of 2,3,4-chloro-substituted β-alkylaminopropiophenone derivatives in CF1 mice and in murine and human tumor cells" (Experimental Report), Anti-Cancer Drugs, 7, 613-620 (1996).
Leone et al., The effects of Melatonin and Melatonin Analogues on the P388, DLD-1 and MCF-7 Tumour Cell Lines, NATO ASI series A: Life Sciences 241-242 (1991).
Malyugina et al.,"Antitumor action of some derivatives of adrenalones," Pharmaceutical Chemistry Journal 13(7): 56-58 (1979).
Messiha and Hughes "Liver Alcohol and Aldehyde Dehydrogenase Inhibition and Potentiation by histamine Agonists and Antagonists," Clinical and Experimental Pharmacology and physiology 6(3) 281-292 (1979).

(56) References Cited

OTHER PUBLICATIONS

Registry (STN) [online], Dec. 21, 1990 (searched date:), CAS Registry No. 131139-67-8.
Registry (STN) [online], Jul. 29, 2001 (searched date: Apr. 25, 2013), CAS Regisrty No. 349438-38-6 Registry (STN) [online], Jun. 5, 2001(searched date:Dec. 19, 2013), CAS Registry No. 339335-56-7.
Werner, W. Et. Al. "Relations between the chemical structure of Mannich bases with and without nitrogen mustard groups and their cytostatic activisty against Ehrlich ascites carcinoma in mice," Arzneimittel-Forschung 20(2): 246-249 (1970).
Werner, W. Et. Al. "Structure-effect interactions in Mannich bases with and without nitrogen-mustard groups and some reduction products derived from β-aminoketones on the basis of a cancerostatic-3-step test with transplantation tumors", Pharmazie, 32(6): 341-347 & CAPLUS Accession No. 1977:545546 (1977).
Weber"Decker-Oxidation 2-Substituierter N-Alkylpyridiniumverbindungen, 5 Mitt. Die Decker-Oxidation Von Homarin", Archly Der Pharmazie, Wiley Verlag, Weinheim, 309(7): 664-669, XP001026698, ISSN: 0365-6233, DOI: 10.1002/ARDP.19763090810 (1976).
White et al. "Specific sequestering agents for the actinides. 16. Synthesis and initial biological testing of polydentate oxohydroxypyridinecarboxylate ligands", Journal of Medical Chemistry, 31(1): 11-18 (1988).
Registry (STN) [online], Apr. 23, 1998, CAS Registry No. 114081-08-2, 3-Pyridinamine, N-(phenylmethyl), 8 pages.
Registry (STN) [online], Oct. 20, 2003 CAS Registry No. 606947-24-4, 4-Oxazolecarbonitrile, 2-[(2-chlorophenoxy) methyl)-5-[[(4-methylphenyl)methyl] amino]-, 8 pages.
Chinn et al., "Isovanillyl Sweeteners. Amide Analogues of Dihydrochalcones," J. Agric. Food Chem.35(3) 409-411 (1987).
Dubois et al., "Dihydrochalcone Sweeteners. A Study of the Atypical Temporal Phenomena," J. Med. Chem. 24(4) 108-428 (1981).
Konoplitskaya et al., "Amides of benzoic and heterocyclic carboxylic acids are inhibitors of rat liver alcohol dehydrogenase," Pharmaceutical Chemistry Journal, 28 (1) 4-7 (1994).
Roe et al., "On the Utility of S-mesitylsulfinimines for the stereoselective synthesis of chiral amines and aziridines," Chem Commun 47 7491-7493 (2011).
Stavber et al. "Selectfluortm F-Teda-Bf4 Mediated Introduction of Perfluoroalkyl-Containing Groups In The Benzylic Position Of Hexamethylbenzene," Acta Chim Slov. 49: 553-560 (2002).

\* cited by examiner 1   msssgtpdlp vlltdlkiqy tkifinnewh dsvsgkkfpv fnpateeelc qveegdkedv
61  dkavkaarqa fqigspwrtm dasergrlly kladlierdr lllatmesmn ggklysnayl
121 sdlagciktl rycagwadki qgrtipidgn fftytrhepi gvcgqiipwn fplvmliwki
181 gpalscgntv vvkpaeqtpl talhvaslik eagfppgvvn ivpgygptag aaisshmdid
241 kvaftgstev gklikeaagk snlkrvtlel ggkspcivla dadldnavef ahhgvfyhqg
301 qcciaasrif veesiydefv rrsverakky ilgnpltpgv tqgpqidkeq ydkildlies
361 gkkegaklec gggpwgnkgy fvqptvfsnv tdemriakee ifgpvqqimk fkslddvikr
421 anntfyglsa gvftkdidka itissalqag tvwvncygvv saqcpfggfk msgngrelge
481 ygfheytevk tvtvkisqkn s (SEQ ID NO:1)

FIG. 5A 1   msssgtpdlp vlltdlkiqy tkifinnewh dsvsgkkfpv fnpateeelc qveegdkedv
61  dkavkaarqa fqigspwrtm dasergrlly kladlierdr lllatmesmn ggklysnayl
121 ndlagciktl rycagwadki qgrtipidgn fftytrhepi gvcgqiipwn fplvmliwki
181 gpalscgntv vvkpaeqtpl talhvaslik eagfppgvvn ivpgygptag aaisshmdid
241 kvaftgstev gklikeaagk snlkrvtlel ggkspcivla dadldnavef ahhgvfyhqg
301 qcciaasrif veesiydefv rrsverakky ilgnpltpgv tqgpqidkeq ydkildlies
361 gkkegaklec gggpwgnkgy fvqptvfsnv tdemriakee ifgpvqqimk fkslddvikr
421 anntfyglsa gvftkdidka itissalqag tvwvncygvv saqcpfggfk msgngrelge
481 ygfheytevk tvtvkisqkn s (SEQ ID NO:2)

FIG. 5B

```
  1 mskiseavkr apaafssgrt rplqfriqql ealqrliqeq eqelvgalaa dlhknewnay
 61 yeevvyvlee ieymiqklpe waadepvekt pqtqqdelyi hseplgvvlv igtwnypfnl
121 tiqpmvgaia agnsvvlkps elsenmasll atiipqyldk dlypvinggv pettelker
181 fdhilytgst gvgkiimtaa akhltpvtle lggkspcyvd kncdldvacr riawgkfmns
241 gqtcvapdyi lcdpsiqnqi veklkkslke fygedakksr dygriisarh fqrvmglieg
301 qkvayggtgd aatryiapti ltdvdpqspv mqeeifgpvl pivcvrslee aiqfinqrek
361 plalymfssn dkvikkmiae tssggvaand vivhitlhsl pfggvgnsgm gsyhgkksfe
421 tfshrrsclv rplmndeglk vryppspakm tqh (SEQ ID NO:3)
```

FIG. 6

```
  1 matangaven gqpdgkppal prpirnlevk ftkifinnew hesksgkkfa tcnpstreqi
 61 ceveegdkpd vdkaveaaqv afqrgspwrr ldalsrgrll hqladlverd ratlaaletm
121 dtgkpflhaf fidlegcirt lryfagwadk iqqktiptdd nvvcftrhep igvcgaitpw
181 nfpllmlvwk lapalccgnt mvlkpaeqtp ltalylgsli keagfppgvv nivpgfgptv
241 gaaisshpqi nkiaftgste vgklvkeaas rsnlkrvtle lggknpcivc adadldlave
301 cahqgvffnq gqcctaasrv fveeqvysef vrrsveyakk rpvgdpfdvk teqgpqidqk
361 qfdkilelie sgkkegakle cggsamedkg lfikptvfse vtdnmriake eifgpvqpil
421 kfksieevik ranstdyglt aavftknldk alklasales gtvwincyna lyaqapfggf
481 kmsgngrelg eyalaeytev ktvtiklgdk np (SEQ ID NO:4)
```

FIG. 7A

```
  1 mattngaven gqpdgkppal prpirnlevk ftkifinndw hesksgrkfa tynpstleki
 61 ceveegdkpd vdkaveaaqa afqrgspwrr ldalsrgqll hqladlverd railatletm
121 dtgkpflhaf fvdlegcikt fryfagwadk iqqrtiptdd nvvcftrhep igvcgaitpw
181 nfpllmlawk lapalccgnt vvlkpaeqtp ltalylasli kevgfppgvv nivpgfgptv
241 gaaisshpqi nkiaftgste vgklvreaas rsnlkrvtle lggknpcivc adadldlave
301 cahqgvffnq gqcctaasrv fveeqvygef vrrsvefakk rpvgdpfdak teqgpqidqk
361 qfdkilelie sgkkegakle cggsamedrg lfikptvfsd vtdnmriake eifgpvqpil
421 kfknleevik ranstdyglt aavftknldk alklaaales gtvwincyna fyaqapfggf
481 kmsgngrelg eyalaeytev ktvtikleek np (SEQ ID NO:5)
```

FIG. 7B

SEQUENCE LISTING

<160> NUMBER OF SEQ ID NOS: 15

<210> SEQ ID NO 1
<211> LENGTH: 501
<212> TYPE: PRT
<213> ORGANISM: Homo sapiens

<400> SEQUENCE: 1

```
Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Ser Asp Leu Ala Gly Cys Ile Lys
        115                 120                 125

Thr Leu Arg Tyr Cys Ala Gly Trp Ala Asp Lys Ile Gln Gly Arg Thr
    130                 135                 140

Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
        275                 280                 285

Glu Phe Ala His His Gly Val Phe Tyr His Gln Gly Gln Cys Cys Ile
    290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350
```

```
Lys Ile Leu Asp Leu Ile Glu Ser Gly Lys Lys Glu Gly Ala Lys Leu
            355                 360                 365

Glu Cys Gly Gly Gly Pro Trp Gly Asn Lys Gly Tyr Phe Val Gln Pro
370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
            435                 440                 445

Ala Gly Thr Val Trp Val Asn Cys Tyr Gly Val Val Ser Ala Gln Cys
450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500

<210> SEQ ID NO 2
<211> LENGTH: 501
<212> TYPE: PRT
<213> ORGANISM: Homo sapiens

<400> SEQUENCE: 2

Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Asn Asp Leu Ala Gly Cys Ile Lys
        115                 120                 125

Thr Leu Arg Tyr Cys Ala Gly Trp Ala Asp Lys Ile Gln Gly Arg Thr
130                 135                 140

Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
    210                 215                 220
```

-continued

Tyr Gly Pro Thr Ala Gly Ala Ile Ser Ser His Met Asp Ile Asp
225                 230                 235                 240

Lys Val Ala Phe Thr Gly Ser Thr Glu Val Gly Lys Leu Ile Lys Glu
        245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
        275                 280                 285

Glu Phe Ala His His Gly Val Phe Tyr His Gln Gly Gln Cys Cys Ile
290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350

Lys Ile Leu Asp Leu Ile Glu Ser Gly Lys Lys Glu Gly Ala Lys Leu
        355                 360                 365

Glu Cys Gly Gly Gly Pro Trp Gly Asn Lys Gly Tyr Phe Val Gln Pro
370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
        435                 440                 445

Ala Gly Thr Val Trp Val Asn Cys Tyr Gly Val Val Ser Ala Gln Cys
450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500

<210> SEQ ID NO 3
<211> LENGTH: 453
<212> TYPE: PRT
<213> ORGANISM: Homo sapiens

<400> SEQUENCE: 3

Met Ser Lys Ile Ser Glu Ala Val Lys Arg Ala Pro Ala Ala Phe Ser
1               5                   10                  15

Ser Gly Arg Thr Arg Pro Leu Gln Phe Arg Ile Gln Gln Leu Glu Ala
            20                  25                  30

Leu Gln Arg Leu Ile Gln Glu Gln Glu Gln Glu Leu Val Gly Ala Leu
        35                  40                  45

Ala Ala Asp Leu His Lys Asn Glu Trp Asn Ala Tyr Tyr Glu Glu Val
    50                  55                  60

Val Tyr Val Leu Glu Glu Ile Glu Tyr Met Ile Gln Lys Leu Pro Glu
65                  70                  75                  80

Trp Ala Ala Asp Glu Pro Val Glu Lys Thr Pro Gln Thr Gln Gln Asp

```
                        85                  90                  95
Glu Leu Tyr Ile His Ser Glu Pro Leu Gly Val Val Leu Val Ile Gly
                100                 105                 110
Thr Trp Asn Tyr Pro Phe Asn Leu Thr Ile Gln Pro Met Val Gly Ala
                115                 120                 125
Ile Ala Ala Gly Asn Ser Val Val Leu Lys Pro Ser Glu Leu Ser Glu
            130                 135                 140
Asn Met Ala Ser Leu Leu Ala Thr Ile Ile Pro Gln Tyr Leu Asp Lys
145                 150                 155                 160
Asp Leu Tyr Pro Val Ile Asn Gly Gly Val Pro Glu Thr Thr Glu Leu
                165                 170                 175
Leu Lys Glu Arg Phe Asp His Ile Leu Tyr Thr Gly Ser Thr Gly Val
                180                 185                 190
Gly Lys Ile Ile Met Thr Ala Ala Ala Lys His Leu Thr Pro Val Thr
                195                 200                 205
Leu Glu Leu Gly Gly Lys Ser Pro Cys Tyr Val Asp Lys Asn Cys Asp
            210                 215                 220
Leu Asp Val Ala Cys Arg Arg Ile Ala Trp Gly Lys Phe Met Asn Ser
225                 230                 235                 240
Gly Gln Thr Cys Val Ala Pro Asp Tyr Ile Leu Cys Asp Pro Ser Ile
                245                 250                 255
Gln Asn Gln Ile Val Glu Lys Leu Lys Lys Ser Leu Lys Glu Phe Tyr
                260                 265                 270
Gly Glu Asp Ala Lys Lys Ser Arg Asp Tyr Gly Arg Ile Ile Ser Ala
                275                 280                 285
Arg His Phe Gln Arg Val Met Gly Leu Ile Glu Gly Gln Lys Val Ala
            290                 295                 300
Tyr Gly Gly Thr Gly Asp Ala Ala Thr Arg Tyr Ile Ala Pro Thr Ile
305                 310                 315                 320
Leu Thr Asp Val Asp Pro Gln Ser Pro Val Met Gln Glu Glu Ile Phe
                325                 330                 335
Gly Pro Val Leu Pro Ile Val Cys Val Arg Ser Leu Glu Glu Ala Ile
                340                 345                 350
Gln Phe Ile Asn Gln Arg Glu Lys Pro Leu Ala Leu Tyr Met Phe Ser
            355                 360                 365
Ser Asn Asp Lys Val Ile Lys Lys Met Ile Ala Glu Thr Ser Ser Gly
            370                 375                 380
Gly Val Ala Ala Asn Asp Val Ile Val His Ile Thr Leu His Ser Leu
385                 390                 395                 400
Pro Phe Gly Gly Val Gly Asn Ser Gly Met Gly Ser Tyr His Gly Lys
                405                 410                 415
Lys Ser Phe Glu Thr Phe Ser His Arg Arg Ser Cys Leu Val Arg Pro
                420                 425                 430
Leu Met Asn Asp Glu Gly Leu Lys Val Arg Tyr Pro Pro Ser Pro Ala
                435                 440                 445
Lys Met Thr Gln His
                450

<210> SEQ ID NO 4
<211> LENGTH: 512
<212> TYPE: PRT
<213> ORGANISM: Homo sapiens

<400> SEQUENCE: 4
```

```
Met Ala Thr Ala Asn Gly Ala Val Glu Asn Gly Gln Pro Asp Gly Lys
1               5                   10                  15

Pro Pro Ala Leu Pro Arg Pro Ile Arg Asn Leu Glu Val Lys Phe Thr
            20                  25                  30

Lys Ile Phe Ile Asn Asn Glu Trp His Glu Ser Lys Ser Gly Lys Lys
                35                  40                  45

Phe Ala Thr Cys Asn Pro Ser Thr Arg Glu Gln Ile Cys Glu Val Glu
            50                  55                  60

Glu Gly Asp Lys Pro Asp Val Asp Lys Ala Val Glu Ala Ala Gln Val
65                  70                  75                  80

Ala Phe Gln Arg Gly Ser Pro Trp Arg Arg Leu Asp Ala Leu Ser Arg
                85                  90                  95

Gly Arg Leu Leu His Gln Leu Ala Asp Leu Val Glu Arg Asp Arg Ala
            100                 105                 110

Thr Leu Ala Ala Leu Glu Thr Met Asp Thr Gly Lys Pro Phe Leu His
            115                 120                 125

Ala Phe Phe Ile Asp Leu Glu Gly Cys Ile Arg Thr Leu Arg Tyr Phe
            130                 135                 140

Ala Gly Trp Ala Asp Lys Ile Gln Gly Lys Thr Ile Pro Thr Asp Asp
145                 150                 155                 160

Asn Val Val Cys Phe Thr Arg His Glu Pro Ile Gly Val Cys Gly Ala
                165                 170                 175

Ile Thr Pro Trp Asn Phe Pro Leu Leu Met Leu Val Trp Lys Leu Ala
            180                 185                 190

Pro Ala Leu Cys Cys Gly Asn Thr Met Val Leu Lys Pro Ala Glu Gln
            195                 200                 205

Thr Pro Leu Thr Ala Leu Tyr Leu Gly Ser Leu Ile Lys Glu Ala Gly
            210                 215                 220

Phe Pro Pro Gly Val Val Asn Ile Val Pro Gly Phe Gly Pro Thr Val
225                 230                 235                 240

Gly Ala Ala Ile Ser Ser His Pro Gln Ile Asn Lys Ile Ala Phe Thr
                245                 250                 255

Gly Ser Thr Glu Val Gly Lys Leu Val Lys Glu Ala Ala Ser Arg Ser
            260                 265                 270

Asn Leu Lys Arg Val Thr Leu Glu Leu Gly Gly Lys Asn Pro Cys Ile
            275                 280                 285

Val Cys Ala Asp Ala Asp Leu Asp Leu Ala Val Glu Cys Ala His Gln
            290                 295                 300

Gly Val Phe Phe Asn Gln Gly Gln Cys Cys Thr Ala Ala Ser Arg Val
305                 310                 315                 320

Phe Val Glu Glu Gln Val Tyr Ser Glu Phe Val Arg Arg Ser Val Glu
                325                 330                 335

Tyr Ala Lys Lys Arg Pro Val Gly Asp Pro Phe Asp Val Lys Thr Glu
            340                 345                 350

Gln Gly Pro Gln Ile Asp Gln Lys Gln Phe Asp Lys Ile Leu Glu Leu
            355                 360                 365

Ile Glu Ser Gly Lys Lys Glu Gly Ala Lys Leu Glu Cys Gly Gly Ser
            370                 375                 380

Ala Met Glu Asp Lys Gly Leu Phe Ile Lys Pro Thr Val Phe Ser Glu
385                 390                 395                 400

Val Thr Asp Asn Met Arg Ile Ala Lys Glu Glu Ile Phe Gly Pro Val
                405                 410                 415

Gln Pro Ile Leu Lys Phe Lys Ser Ile Glu Glu Val Ile Lys Arg Ala
```

```
            420                 425                 430
Asn Ser Thr Asp Tyr Gly Leu Thr Ala Ala Val Phe Thr Lys Asn Leu
        435                 440                 445
Asp Lys Ala Leu Lys Leu Ala Ser Ala Leu Glu Ser Gly Thr Val Trp
    450                 455                 460
Ile Asn Cys Tyr Asn Ala Leu Tyr Ala Gln Ala Pro Phe Gly Gly Phe
465                 470                 475                 480
Lys Met Ser Gly Asn Gly Arg Glu Leu Gly Glu Tyr Ala Leu Ala Glu
                485                 490                 495
Tyr Thr Glu Val Lys Thr Val Thr Ile Lys Leu Gly Asp Lys Asn Pro
            500                 505                 510

<210> SEQ ID NO 5
<211> LENGTH: 512
<212> TYPE: PRT
<213> ORGANISM: Mus musculus

<400> SEQUENCE: 5

Met Ala Thr Thr Asn Gly Ala Val Glu Asn Gly Gln Pro Asp Gly Lys
1               5                   10                  15
Pro Pro Ala Leu Pro Arg Pro Ile Arg Asn Leu Glu Val Lys Phe Thr
            20                  25                  30
Lys Ile Phe Ile Asn Asn Asp Trp His Glu Ser Lys Ser Gly Arg Lys
        35                  40                  45
Phe Ala Thr Tyr Asn Pro Ser Thr Leu Glu Lys Ile Cys Glu Val Glu
    50                  55                  60
Glu Gly Asp Lys Pro Asp Val Asp Lys Ala Val Glu Ala Ala Gln Ala
65                  70                  75                  80
Ala Phe Gln Arg Gly Ser Pro Trp Arg Arg Leu Asp Ala Leu Ser Arg
                85                  90                  95
Gly Gln Leu Leu His Gln Leu Ala Asp Leu Val Glu Arg Asp Arg Ala
            100                 105                 110
Ile Leu Ala Thr Leu Glu Thr Met Asp Thr Gly Lys Pro Phe Leu His
        115                 120                 125
Ala Phe Phe Val Asp Leu Glu Gly Cys Ile Lys Thr Phe Arg Tyr Phe
    130                 135                 140
Ala Gly Trp Ala Asp Lys Ile Gln Gly Arg Thr Ile Pro Thr Asp Asp
145                 150                 155                 160
Asn Val Val Cys Phe Thr Arg His Glu Pro Ile Gly Val Cys Gly Ala
                165                 170                 175
Ile Thr Pro Trp Asn Phe Pro Leu Leu Met Leu Ala Trp Lys Leu Ala
            180                 185                 190
Pro Ala Leu Cys Cys Gly Asn Thr Val Val Leu Lys Pro Ala Glu Gln
        195                 200                 205
Thr Pro Leu Thr Ala Leu Tyr Leu Ala Ser Leu Ile Lys Glu Val Gly
    210                 215                 220
Phe Pro Pro Gly Val Val Asn Ile Val Pro Gly Phe Gly Pro Thr Val
225                 230                 235                 240
Gly Ala Ala Ile Ser Ser His Pro Gln Ile Asn Lys Ile Ala Phe Thr
                245                 250                 255
Gly Ser Thr Glu Val Gly Lys Leu Val Arg Glu Ala Ala Ser Arg Ser
            260                 265                 270
Asn Leu Lys Arg Val Thr Leu Glu Leu Gly Gly Lys Asn Pro Cys Ile
        275                 280                 285
```

```
Val Cys Ala Asp Ala Asp Leu Asp Leu Ala Val Glu Cys Ala His Gln
    290                 295                 300

Gly Val Phe Phe Asn Gln Gly Gln Cys Cys Thr Ala Ala Ser Arg Val
305                 310                 315                 320

Phe Val Glu Glu Gln Val Tyr Gly Glu Phe Val Arg Arg Ser Val Glu
                325                 330                 335

Phe Ala Lys Lys Arg Pro Val Gly Asp Pro Phe Asp Ala Lys Thr Glu
                340                 345                 350

Gln Gly Pro Gln Ile Asp Gln Lys Gln Phe Asp Lys Ile Leu Glu Leu
                355                 360                 365

Ile Glu Ser Gly Lys Lys Glu Gly Ala Lys Leu Glu Cys Gly Gly Ser
370                 375                 380

Ala Met Glu Asp Arg Gly Leu Phe Ile Lys Pro Thr Val Phe Ser Asp
385                 390                 395                 400

Val Thr Asp Asn Met Arg Ile Ala Lys Glu Glu Ile Phe Gly Pro Val
                405                 410                 415

Gln Pro Ile Leu Lys Phe Lys Asn Leu Glu Glu Val Ile Lys Arg Ala
                420                 425                 430

Asn Ser Thr Asp Tyr Gly Leu Thr Ala Ala Val Phe Thr Lys Asn Leu
                435                 440                 445

Asp Lys Ala Leu Lys Leu Ala Ala Ala Leu Glu Ser Gly Thr Val Trp
450                 455                 460

Ile Asn Cys Tyr Asn Ala Phe Tyr Ala Gln Ala Pro Phe Gly Gly Phe
465                 470                 475                 480

Lys Met Ser Gly Asn Gly Arg Glu Leu Gly Glu Tyr Ala Leu Ala Glu
                485                 490                 495

Tyr Thr Glu Val Lys Thr Val Thr Ile Lys Leu Glu Glu Lys Asn Pro
                500                 505                 510

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
cggctaccac atccaaggaa                                              20

<210> SEQ ID NO 7
<211> LENGTH: 18
<212> TYPE: DNA
<213> ORGANISM: Artificial sequence
<220> FEATURE:
<223> OTHER INFORMATION: Synthetic primer

<400> SEQUENCE: 7
gctggaatta ccgcggct                                                18

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
gcacgccaga cttacctgtc                                              20
```

```
<210> SEQ ID NO 9
<211> LENGTH: 20
<212> TYPE: DNA
<213> ORGANISM: Artificial sequence
<220> FEATURE:
<223> OTHER INFORMATION: Synthetic primer

<400> SEQUENCE: 9
ccactcactg aatcatgcca                                                  20

<210> SEQ ID NO 10
<211> LENGTH: 19
<212> TYPE: DNA
<213> ORGANISM: Artificial sequence
<220> FEATURE:
<223> OTHER INFORMATION: Synthetic primer

<400> SEQUENCE: 10
gaaaccatcc ccattgact                                                   19

<210> SEQ ID NO 11
<211> LENGTH: 21
<212> TYPE: DNA
<213> ORGANISM: Artificial sequence
<220> FEATURE:
<223> OTHER INFORMATION: Synthetic primer

<400> SEQUENCE: 11
gtctgctcag ctaccttcat c                                                21

<210> SEQ ID NO 12
<211> LENGTH: 20
<212> TYPE: DNA
<213> ORGANISM: Artificial sequence
<220> FEATURE:
<223> OTHER INFORMATION: Synthetic primer

<400> SEQUENCE: 12
atcaactgct acaacgccct                                                  20

<210> SEQ ID NO 13
<211> LENGTH: 20
<212> TYPE: DNA
<213> ORGANISM: Artificial sequence
<220> FEATURE:
<223> OTHER INFORMATION: Synthetic primer

<400> SEQUENCE: 13
tattcggcca aagcgtattc                                                  20

<210> SEQ ID NO 14
<211> LENGTH: 21
<212> TYPE: DNA
<213> ORGANISM: Artificial sequence
<220> FEATURE:
<223> OTHER INFORMATION: Synthetic primer

<400> SEQUENCE: 14
cgctcaactc tttcccattt g                                                21

<210> SEQ ID NO 15
<211> LENGTH: 20
<212> TYPE: DNA
<213> ORGANISM: Artificial sequence
<220> FEATURE:
<223> OTHER INFORMATION: Synthetic primer
```

```
<400> SEQUENCE: 15
ttccccaatc cacctttgac                                        20
```

COMPOSITIONS AND METHODS FOR INCREASING PROLIFERATION OF ADULT SALIVARY STEM CELLS

CROSS-REFERENCE

This application claims the benefit of U.S. Provisional Patent Application No. 61/480,506, filed Apr. 29, 2011, which application is incorporated herein by reference in its entirety.

STATEMENT REGARDING FEDERALLY SPONSORED RESEARCH

This invention was made with government support under Grant No. AA011147 awarded by the National Institutes of Health. The government has certain rights in the invention.

BACKGROUND

Most head and neck cancer (HNC) patients receive radiotherapy (RT) as part of their cancer management. Radiation exposure results in permanent damage to the salivary glands, causing loss of function and subsequent RT-related xerostomia or dry mouth. Patients with RT xerostomia experience reduced quality and quantity of saliva, which leads to considerable morbidities, including solid food dysphagia, chronic dental caries, recurrent oral infections and rare mandibular osteoradionecrosis. It is estimated that >80% of patients receiving head and neck RT suffer from many of these side effects. Current approved medical managements for RT xerosomia include the use of salivary substitutes, lubricants and cholinergic agonists to stimulate salivary secretion. These treatments remain palliative in nature, require chronic use and are often ineffective. Intensity modulated radiotherapy (IMRT) can protect the parotid glands from direct radiation injury in selective cases; however, it often cannot spare the submandibular glands (SMG), which are responsible for resting saliva production. The vicinity of the SMG to the level II nodes, which are the most commonly involved nodes in HNC, makes it harder to spare them from direct RT beams. At least one randomized study indicated that although IMRT resulted in improved parotid sparing and more stimulatory saliva production, it did not result in significant improvement of patient's subjective xerostomia. In contrast, SMG transfer and sparing from direct RT beams was associated with a significantly better subjective xerostomia function as assessed by xerostomia and quality of life questionnaires. Therefore, despite widespread IMRT use in HNC, development of methods to reconstitute salivary gland tissue, specifically SMG, and recovery of physiological salivary secretion after RT is needed in HNC patients.

LITERATURE

U.S. Publication No. 2010/0113423; WO 2010/062308; U.S. Publication No. US 2010/0063100; WO 2010/028175; Lombaert et al. (2008) PLoS ONE 3(4):e2063.

SUMMARY OF THE INVENTION

The present disclosure provides methods of increasing proliferation of adult salivary stem cells. The methods include contacting adult salivary stem cells in vivo, in vitro, or ex vivo with an aldehyde dehydrogenase (ALDH) agonist. Increasing proliferation of adult salivary stem cells can be carried out to provide for an increase in the number of adult salivary stem cells in an individual undergoing radiotherapy for head and neck cancer.

BRIEF DESCRIPTION OF THE DRAWINGS

FIG. 5A and FIG. 5B provide exemplary ALDH1 amino acid sequences.

FIG. 6 provides an exemplary ALDH3 amino acid sequence.

FIG. 7A and FIG. 7B provide exemplary ALDH6 amino acid sequences.

DEFINITIONS

Figure 1A:
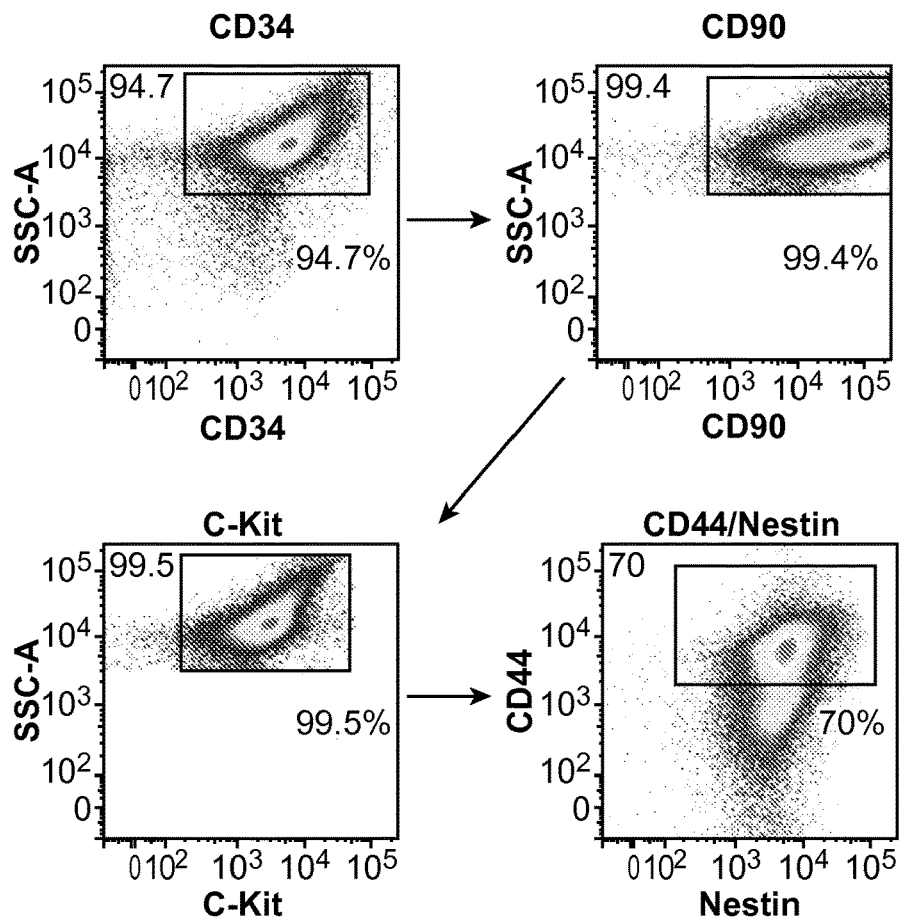
FIG. 1A shows the results of flow cytometric analysis of isolated human salivary stem cells.

As used herein, the term "aldehyde dehydrogenase" or "ALDH" refers to an enzyme that oxidizes an aldehyde to its corresponding acid in an NAD+-dependent or an NADP+-dependent reaction. The term "ALDH" encompasses any of the known ALDH isozymes, including ALDH1, ALDH2, ALDH3, ALDH4, ALDH5, ALDH6, etc.

As used herein, "ALDH1" refers to a cytosolic aldehyde dehydrogenase that oxidizes an aldehyde to its corresponding acid in an NAD+-dependent reaction.

The term "ALDH1" encompasses ALDH1 from various species. Amino acid sequences of ALDH1 from various species are publicly available. See, e.g., GenBank Accession Nos. AAC51652 (*Homo sapiens* ALDH1); NP_000680 (*Homo sapiens* ALDH1); AAH61526 (*Rattus norvegicus* ALDH1); AAI05194 (*Bos taurus* ALDH1); and NP_036051 (*Mus musculus* ALDH1). The term "ALDH1" as used herein also encompasses fragments, fusion proteins, and variants (e.g., variants having one or more amino acid substitutions, addition, deletions, and/or insertions) that retain ALDH1 enzymatic activity. The term "ALDH1" encompasses an aldehyde dehydrogenase that oxidizes aromatic aldehydes, including those of the retinaldehyde, naphthaldehyde, phenanthrenealdehyde, and coumarinaldehyde series, as well as complex polyaromatic aldehydes. The term "ALDH1" encompasses a cytosolic aldehyde dehydrogenase.

The term "ALDH1" encompasses an enzymatically active polypeptide having at least about 75%, at least about 80%, at least about 85%, at least about 90%, at least about 95%, at least about 98%, at least about 99%, or 100%, amino acid sequence identity to an amino acid sequence depicted in FIG. 5A (SEQ ID NO:1) or FIG. 5B (SEQ ID NO:2).

The term "ALDH3" encompasses ALDH3 from various species. Amino acid sequences of ALDH3 from various species are publicly available. See, e.g., GenBank Accession Nos. AAB26658 (*Homo sapiens* ALDH3), NP_000683 (*Homo sapiens* ALDH3), P30838 (*Homo sapiens* ALDH3), NP_001106196 (*Mus musculus* ALDH3), and AAH70924 (*Rattus norvegicus* ALDH3). The term "ALDH3" as used herein also encompasses fragments, fusion proteins, and variants (e.g., variants having one or more amino acid substitutions, addition, deletions, and/or insertions) that retain ALDH3 enzymatic activity. The term "ALDH3" encompasses an aldehyde dehydrogenase that exhibits specificity toward aromatic aldehydes, e.g., oxidizing aromatic aldehydes of the 2-naphthaldehyde series, but inactive toward 1-naphthaldehydes and higher polyaromatic aldehydes. The term "ALDH3" encompasses an aldehyde dehydrogenase that can use both NAD+ and NADP+ as co-substrate. The term "ALDH3" encompasses aldehyde dehydrogenase found naturally in the stomach, in the lung, in saliva, and in the cornea.

The term "ALDH3" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence depicted in FIG. 6 (SEQ ID NO:3).

The term "ALDH6" (also referred to as "aldehyde dehydrogenase family 1 member A3" or "ALDH1A3") encompasses ALDH6 from various species. Amino acid sequences of ALDH6 from various species are publicly available. See, e.g., GenBank Accession Nos. AAA79036.1 (*Homo sapiens* ALDH6), NP_000684.2 (*Homo sapiens* ALDH6) (FIG. 3A), P47895 (*Homo sapiens* ALDH6), AAG33935.1 (*Mus musculus* ALDH6), NP_444310.3 (*Mus musculus* ALDH6) (FIG. 3B), and NP_695212.1 (*Rattus norvegicus* ALDH6). The term "ALDH6" as used herein also encompasses fragments, fusion proteins, and variants (e.g., variants having one or more amino acid substitutions, addition, deletions, and/or insertions) that retain ALDH6 enzymatic activity. The term "ALDH6" encompasses an aldehyde dehydrogenase that exhibits specificity toward free retinal and cellular retinol-binding protein-bound retinal, and oxidizes retinal to form all-trans-retinoic acid (RA). The term "ALDH6" encompasses aldehyde dehydrogenase found naturally, e.g., in keratinocytes, in saliva, in salivary gland, in breast epithelium, in stomach, in kidney, etc.

The term "ALDH6" encompasses an enzymatically active polypeptide having at least about 75%, at least about 80%, at least about 85%, at least about 90%, at least about 95%, at least about 98%, at least about 99%, or 100%, amino acid sequence identity to an amino acid sequence depicted in FIG. 7A (SEQ ID NO:4) or 7B (SEQ ID NO:5).

The terms "subject," "individual," and "patient" are used interchangeably herein to a member or members of any mammalian or non-mammalian species that may have a need for the pharmaceutical methods, compositions and treatments described herein. Subjects and patients thus include, without limitation, primate (including humans and non-human primates), canine, feline, ungulate (e.g., equine, bovine, swine (e.g., pig)), avian, and other subjects. Humans and non-human mammals having commercial importance (e.g., livestock and domesticated animals) are of particular interest.

"Mammal" refers to a member or members of any mammalian species, and includes, by way of example, canines; felines; equines; bovines; ovines; rodentia, etc. and primates, e.g., humans. Non-human animal models, particularly mammals, e.g. a non-human primate, a murine (e.g., a mouse, a rat), lagomorpha, etc. may be used for experimental investigations.

The term "isolated compound" means a compound which has been substantially separated from, or enriched relative to, other compounds with which it occurs in nature. Isolated compounds are at least about 80%, at least about 90% pure, at least about 98% pure, or at least about 99% pure, by weight. The present disclosure is meant to comprehend diastereomers as well as their racemic and resolved, enantiomerically pure forms and pharmaceutically acceptable salts thereof.

A "therapeutically effective amount" or "efficacious amount" means the amount of a compound that, when administered to a mammal or other subject for treating a disease or condition, is sufficient, in combination with another agent, or alone in one or more doses, to effect such treatment for the disease or condition. The "therapeutically effective amount" will vary depending on the compound, the disease and its severity and the age, weight, etc., of the subject to be treated.

A "pro-drug" means any compound that releases an active parent drug according to one or more of the generic formulas shown below in vivo when such pro-drug is administered to a mammalian subject or mammalian cells. Pro-drugs of a compound of one or more of the generic formulas shown below are prepared by modifying functional groups present in the compound of the generic formula in such a way that the modifications may be cleaved in vivo to release the parent compound. Pro-drugs include compounds of one or more of the generic formulas shown below wherein a hydroxy, amino, or sulfhydryl group in one or more of the generic formulas shown below is bonded to any group that may be cleaved in vivo to regenerate the free hydroxyl, amino, or sulfhydryl group, respectively. Examples of pro-drugs include, but are not limited to esters (e.g., acetate, formate, and benzoate derivatives), carbamates (e.g., N,N-dimethylaminocarbonyl) of hydroxy functional groups in compounds of one or more of the generic formulas shown below, and the like.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

"In combination with," or "co-administration," as used herein, in the context of administering a first compound and at least a second compound, refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "unit dosage form," as used herein, refers to physically discrete units suitable as unitary dosages for human and animal subjects, each unit containing a predetermined quantity of a compound, calculated in an amount sufficient to produce the desired effect in association with a pharmaceutically acceptable diluent, carrier or vehicle. The specifications for a dosage form may depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a compound (e.g., an ALDH agonist) and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C=C(OR) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

The term "organic group" and "organic radical" as used herein means any carbon-containing group, including hydrocarbon groups that are classified as an aliphatic group, cyclic group, aromatic group, functionalized derivatives thereof and/or various combinations thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, isopropyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, trifloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(iso-propoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy) phenyl group such as 2, 3 or 4-carboxyphenyl or 2,4-di (protected carboxy)phenyl; a mono- or di(hydroxymethyl) phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl) alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

A compound may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an ALDH3 agonist" includes a plurality of such agonists and reference to "the adult salivary stem cell" includes reference to one or more such stem cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of increasing proliferation of adult salivary stem cells. The present disclosure provides methods of increasing the number of adult salivary stem cells in an individual. The methods generally involve contacting adult salivary stem cells in vivo, in vitro, or ex vivo with an aldehyde dehydrogenase (ALDH) agonist. Contacting the adult salivary stem cells with the ALDH agonist increases the number of adult salivary stem cells and generates an expanded population of adult salivary stem cells.

Methods of Increasing Proliferation of Adult Salivary Cells

The present disclosure methods of increasing proliferation of adult salivary stem cells, the methods including contacting adult salivary stem cells in vivo, in vitro, or ex vivo with an ALDH agonist. Suitable ALDH agonists include compounds that increase the activity of one or more of ALDH1, ALDH3, and ALDH6.

According to one embodiment, a subject method involves contacting adult salivary stem cells in vitro, in vivo, or ex vivo with an effective amount of an ALDH1 agonist (e.g., a natural or synthetic ALDH1 agonist), wherein the contacting increases the number of adult salivary stem cells by at least about 10%, thereby generating an expanded population of adult salivary stem cells. In certain aspects, the ALDH1 agonist increases the number of adult salivary stem cells by at least 10%, at least 15%, at least 20%, at least 25%, at least 40%, at least 50%, at least 75%, at least 2-fold, at least 2.5-fold, at least 5-fold, at least 10-fold, or more than 10-fold, compared to the number of adult salivary stem cells not contacted with the ALDH1 agonist.

According to one embodiment, a subject method involves contacting adult salivary stem cells in vitro, in vivo, or ex vivo with an effective amount of an ALDH3 agonist (e.g., a natural or synthetic ALDH3 agonist), wherein the contacting increases the number of adult salivary stem cells by at least about 10%, thereby generating an expanded population of adult salivary stem cells. In certain aspects, the ALDH3 agonist increases the number of adult salivary stem cells by at least 10%, at least 15%, at least 20%, at least 25%, at least 40%, at least 50%, at least 75%, at least 2-fold, at least 2.5-fold, at least 5-fold, at least 10-fold, or more than 10-fold, compared to the number of adult salivary stem cells not contacted with the ALDH3 agonist.

According to one embodiment, a subject method involves contacting adult salivary stem cells in vitro, in vivo, or ex vivo with an effective amount of an ALDH6 agonist (e.g., a natural or synthetic ALDH6 agonist), wherein the contacting increases the number of adult salivary stem cells by at least about 10%, thereby generating an expanded population of adult salivary stem cells. In certain aspects, the ALDH6 agonist increases the number of adult salivary stem cells by at least 10%, at least 15%, at least 20%, at least 25%, at least 40%, at least 50%, at least 75%, at least 2-fold, at least 2.5-fold, at least 5-fold, at least 10-fold, or more than 10-fold, compared to the number of adult salivary stem cells not contacted with the ALDH6 agonist.

Increasing the number of adult salivary stem cells is useful for treating an individual who has undergone, or is about to undergo, radiation treatment for a head and neck cancer. Increasing the number of adult salivary stem cells in an individual provides for an increase in the number of adult salivary stem cells in the individual following radiation treatment, and also provides for an increase in the number of functional saliva-producing cells in the individual following radiation treatment. For example, a subject method provides for an increase in the number of functional saliva-producing cells in an individual following radiation treatment for a head and neck cancer of at least 10%, at least 15%, at least 20%, at least 25%, at least 40%, at least 50%, at least 75%, at least 2-fold, at least 2.5-fold, at least 5-fold, at least 10-fold, or more than 10-fold, compared to the number of functional saliva-producing cells in the individual in the absence of treatment with a subject method.

As noted above, in some cases, a subject method is carried out in vitro. Thus, e.g., adult salivary stem cells can be contacted with an ALDH agonist in vitro to increase the number of adult salivary stem cells.

In some cases, a subject method is carried out ex vivo, e.g., adult salivary stem cells are obtained from a donor individual, the adult salivary stem cells are expanded ex vivo by contacting the adult salivary stem cells with one or more ALDH1, ALDH3, or ALDH6 agonists, to produce an ex vivo expanded population of donor adult salivary stem cells. The ex vivo expanded population of donor adult salivary stem cells is introduced into a recipient individual, e.g., an individual who has head and neck cancer who has undergone radiation treatment for the cancer. In some instances, the donor individual is the same as the recipient individual, e.g., adult salivary stem cells are obtained from the donor individual before the donor individual undergoes radiation treatment for a head and neck cancer, the adult salivary stem cells are expanded ex vivo, as described above, and the ex vivo expanded donor salivary stem cell population is introduced into the donor individual (who is now the recipient) after the donor has undergone radiation treatment for the head and neck cancer. In other embodiments, the donor individual and the recipient individual are not the same individual.

A subject method can be carried out in vivo. For example, one or more ALDH1, ALDH3, or ALDH6 agonist is administered to an individual before and/or after radiation treatment for a head and neck cancer.

Isolation and Maintenance of Adult Salivary Stem Cells

A number of approaches for isolating and culturing adult salivary stem cells are known in the art, and any such method can be used to obtain adult salivary stem cells for use in a subject method. For example, human salivary gland tissue may be isolated and cultured as described by Szlavik et al. (Tissue Eng. Part A (2008) 14:1915-26); and Rotter N. et al. (Stem Cells Dev. (2008) 17:509-518), the disclosures of which are incorporated herein by reference in their entireties. Human salivary stem cells can be isolated from tissues such as the submandibular gland and/or the parotid gland.

According to one aspect of the present disclosure, salivary gland tissue isolated from a donor individual is minced and dissociated in an appropriate cell dissociation medium, centrifuged, filtered, and resuspended in a medium with one or more growth factors (e.g., epidermal growth factor (EGF), fibroblast growth factor 2 (FGF2), insulin-like growth factor-1 (IGF-1), and the like), antibiotics, and so forth to support maintenance and viability of the dissociated cells. Optionally, the stem cells are isolated or enriched from the primary cell suspension. This may be achieved by contacting the donor adult salivary stem cells in vitro with a reagent (e.g., an antibody) that specifically recognizes a marker associated with adult salivary stem cells, where contacting the donor adult salivary stem cells with the reagent is performed prior to contacting the donor adult salivary stem cells with the ALDH agonist.

Useful markers for salivary stem cells include CD34, CD90, c-Kit, CD44, Nestin, CD49f, ALDH1, and combinations thereof. For example, human and mouse adult salivary stem cells may be isolated by selecting for CD34-positive and cKit-positive cells, respectively, e.g., using the EASY-SEP™ positive selection kit (STEMCELL Technologies, Inc., Vancouver, BC). Detection of markers such as CD49f can be achieved using antibody specific for the marker, where the antibody can comprise a detectable label. Standard methods such as fluorescence activated cell sorting (FACS) can be used to isolate the cells. ALDH expression can be detected using ALDEFLUOR® aldehyde dehydrogenase fluorescent detection label. For example, ALDH converts the ALDH substrate, BAAA (BODIPY-aminoacetaldehyde), into the fluorescent product BAA (BODIPY-aminoacetate). Cells expressing high levels of ALDH become brightly fluorescent and can be identified using standard flow cytometry methods and/or isolated by cell sorting. See, e.g., Deng et al. (2010) *PLoS One* 5:e10277.

Isolation and culture of mouse salivary stem cells is described in, e.g., Lombaert et al. (2008) *PLoS One* 3:e2063. Isolation and culture of human salivary stem cells is also described in Lombaert et al. (2008) supra.

In certain aspects, adult salivary stem cells (isolated or otherwise) may be maintained in a culture medium prior to being contacted with the ALDH agonist. For example, the cells may be maintained in a medium that includes one or more factors that prevents the salivary stem cells from differentiating into more specialized cells.

According to one embodiment, the donor adult salivary stem cells are obtained from an individual (e.g., having a head and neck cancer) prior to that individual undergoing a radiation treatment, e.g., radiotherapy to treat a head and neck cancer. In other aspects, the donor adult stem cells are obtained from an individual other than a recipient individual, e.g., an individual who neither has cancer nor is undergoing radiation treatment.

Contacting Adult Salivary Stem Cells with an ALDH Agonist in vitro

As noted above, in some cases, a subject method is carried out in vitro. Methods of the present disclosure include contacting adult salivary stem cells in vitro with an ALDH agonist, which ALDH agonist may be, e.g., an activator of one or more of ALDH1, ALDH3, and ALDH6. In the case of contacting adult salivary stem cells with an ALDH agonist in vitro, the cell culture medium may be supplemented with an effective amount of the agonist. The cell culture medium may be chosen such that the medium is compatible with the agonist, e.g., the agonist is stable and active in the medium. The medium may be supplemented with one or more components that enhance the stability and/or activity of the ALDH agonist.

Contacting Adult Salivary Stem Cells with an ALDH Agonist ex vivo

In some cases, a subject method is carried out ex vivo, e.g., adult salivary stem cells are obtained from a donor individual, the adult salivary stem cells are expanded ex vivo by contacting the adult salivary stem cells with one or more ALDH1, ALDH3, or ALDH6 agonists, to produce an ex vivo expanded population of donor adult salivary stem cells. The ex vivo expanded population of donor adult salivary stem cells is introduced into a recipient individual, e.g., an individual who has head and neck cancer who has undergone radiation treatment for the cancer. An ex vivo expanded adult salivary stem cell population can be obtained by culturing adult salivary stem cells ex vivo in a culture medium comprising one or more ALDH1, ALDH3, or ALDH6 agonists, where the culturing can take place for about 4 hours to about 72 hours, e.g., from about 4 hours to about 8 hours, from about 8 hours to about 16 hours, from about 16 hours to about 24 hours, from about 24 hours to about 36 hours, from about 36 hours to about 48 hours, or from about 48 hours to about 72 hours, or more than 72 hours.

In some instances, the donor individual is the same as the recipient individual, in which case the cells are considered autologous. For example, adult salivary stem cells are obtained from the donor individual before the donor individual undergoes radiation treatment for a head and neck cancer, the adult salivary stem cells are expanded ex vivo, as described above, and the ex vivo expanded donor salivary stem cell population is introduced into the donor individual (who is now the recipient) after the donor has undergone radiation treatment for the head and neck cancer.

In other embodiments, the donor individual and the recipient individual are not the same individual, in which case the cells are allogeneic. The donor and the recipient can be human leukocyte antigen (HLA) typed before transplantation, and the closest HLA match identified as a suitable donor.

Introducing Salivary Stem Cells into a Recipient Individual

As noted above, methods of the present disclosure optionally include introducing an expanded population of adult salivary stem cells (e.g., where the expansion is generated by contacting the cells with an ALDH agonist, e.g., an ALDH1 agonist and/or an ALDH3 agonist and/or an ALDH6 agonist) into a recipient individual (e.g., a human), where the recipient individual has a head and neck cancer, and where the expanded population of adult salivary stem cells are introduced after the recipient individual has undergone radiation treatment for the cancer. Introduction of the expanded salivary stem cells is useful in a variety of applications, including stem cell-based therapies for restoring function to a salivary gland of an individual who suffers from xerostomia or dry mouth (e.g., radiotherapy-related xerostomia). For example, the introduced (e.g., "transplanted") salivary stem cells may engraft to an irradiated salivary gland and differentiate into functional saliva-producing cells, thereby restoring or enhancing function of the irradiated salivary gland.

In one embodiment, the cells to be introduced into the recipient individual are provided as a suspension, which may be a single cell suspension, or a suspension of small clumps of cells, and which are distinguished from solid tissue grafts, which are implanted and are not injected or infused. The cell suspension is a form that can be injected or infused into a recipient. In another embodiment, the cells are provided as an ex vivo engineered tissue construct. Survival of the cells or tissue may be measured after short periods of time, e.g. after at least about three to about seven days.

The number of salivary stem cells transplanted into a recipient individual can vary from about 10 to about $10^8$, e.g., from 10 to $10^2$, from about $10^2$ to about $10^3$, from about $10^3$ to about $10^4$, from about $10^4$ to about $10^5$, from about $10^5$ to about $10^6$, from about $10^6$ to about $10^7$, or from about $10^7$ to about $10^8$. A population of adult salivary stem cells to be introduced into a recipient individual is generally at least about 75%, at least about 80%, at least about 85%, at least about 90%, at least about 95%, at least about 98%, or more than 98%, adult salivary stem cells.

The adult salivary stem cells to be introduced into the recipient individual may be referred to as a cell transplant. A cell transplant, as used herein, is the transplantation of one or more donor salivary stem cells into a recipient body, usually for the purpose of augmenting function of an organ or tissue in the recipient. The donor stem cells may originate from a salivary gland of the recipient, in which case the donor and the recipient are the same individual. In other aspects, the recipient is an individual to whom tissue or cells from another individual (donor), commonly of the same species, has been transferred. When the donor and recipient are not the same individual, the HLA antigens (or MHC antigens), which may be Class I or Class II, generally will be matched, although one or more of the HLA antigens may be different in the donor as compared to the recipient. The graft recipient and donor are generally mammals, e.g., humans. Laboratory animals, such as rodents, e.g. mice, rats, etc. are of interest. The cells may be allogeneic, autologous, or xenogeneic with respect to the recipient.

The cells may be provided as a suspension, which suspension includes one or more survival factors. As used herein, the term "survival factors" refers to biologically active agents that are provided in a formulation for the suspension of cells prior to transplantation. The presence of survival factor(s) enhances the survival of cells after the cells are transferred into the body of a recipient. Survival factors may be utilized as one or a cocktail of factors. In some embodiments, the survival factors are also utilized as culture additives for a period of time prior to transplantation.

The donor salivary stem cells may be administered in any physiologically acceptable excipient inlcuding an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The cells may be introduced by injection, catheter, or the like. The cells may be frozen at liquid nitrogen temperatures and stored for long periods of time, being capable of use on thawing. If frozen, the cells may be stored, e.g., in a 10% dimethylsulfoxide (DMSO), 50% fetal calf serum (FCS) (or other suitable serum or serum substitute), 40% RPMI 1640 medium (or other suitable culture medium).

The cell formulations may be used for tissue (e.g., salivary gland) reconstitution or regeneration in a human patient or other subject in need of such treatment, e.g., a recipient individual having head and neck cancer who has undergone radiation treatment for the cancer. The cells are administered in a manner that permits them to graft or migrate to the intended tissue site and reconstitute or regenerate the functionally deficient area (e.g., an irradiated salivary gland).

The salivary stem cells may also be genetically modified to enhance survival, control proliferation, and the like. Cells may be genetically altering by transfection or transduction with a suitable vector, homologous recombination, or other appropriate technique, so that they express a gene of interest. For example, cells can be transfected with genes encoding a telomerase catalytic component (TERT), e.g., under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over an 8-16 h period, and then exchanged into growth medium for 1-2 days. Genetically altered cells are selected using a drug selection agent such as puromycin, G418, or blasticidin, and then recultured.

ALDH Agonists

A subject method involves use of compounds that function as activators of ALDH enzymatic activity. Activators of ALDH activity are also referred to herein as ALDH agonists.

In some embodiments, a suitable ALDH agonist selectively modulates (e.g., increases) an enzymatic activity of a particular ALDH isozyme. For example, in some embodiments, a suitable ALDH agonist selectively increases an enzymatic activity of ALDH1. For example, in some embodiments, a suitable ALDH agonist increases an enzymatic activity of ALDH1, but does not substantially increase the same enzymatic activity of an ALDH isozyme other than ALDH1, e.g., the ALDH agonist increases an enzymatic activity of an ALDH isozyme other than ALDH1, if at all, by no more than about 15%, e.g., by less than 15%, less than 10%, less than 5%, or less than 1%.

In some embodiments, a suitable ALDH agonist selectively modulates (e.g., increases) an enzymatic activity of ALDH3. For example, in some embodiments, a suitable ALDH agonist increases an enzymatic activity of ALDH3, but does not substantially increase the same enzymatic activity of an ALDH isozyme other than ALDH3, e.g., the ALDH agonist increases an enzymatic activity of an ALDH isozyme other than ALDH3, if at all, by no more than about 15%, e.g., by less than 15%, less than 10%, less than 5%, or less than 1%.

In some embodiments, a suitable ALDH agonist selectively modulates (e.g., increases) an enzymatic activity of ALDH6. For example, in some embodiments, a suitable ALDH agonist increases an enzymatic activity of ALDH6, but does not substantially increase the same enzymatic activity of an ALDH isozyme other than ALDH6, e.g., the ALDH agonist increases an enzymatic activity of an ALDH isozyme other than ALDH6, if at all, by no more than about 15%, e.g., by less than 15%, less than 10%, less than 5%, or less than 1%.

In some embodiments, a suitable ALDH agonist increases enzymatic activity of both ALDH3 and ALDH1. In some embodiments, a suitable ALDH agonist increases enzymatic activity of both ALDH3 and ALDH1, but does not substantially increase enzymatic activity of an ALDH isozyme other than ALDH3 and ALDH1.

In some embodiments, a suitable ALDH agonist increases enzymatic activity of both ALDH6 and ALDH1. In some embodiments, a suitable ALDH agonist increases enzymatic activity of both ALDH6 and ALDH1, but does not substantially increase enzymatic activity of an ALDH isozyme other than ALDH6 and ALDH1.

In some embodiments, a suitable ALDH agonist increases enzymatic activity of both ALDH6 and ALDH3. In some embodiments, a suitable ALDH agonist increases enzymatic activity of both ALDH6 and ALDH3, but does not substantially increase enzymatic activity of an ALDH isozyme other than ALDH6 and ALDH3.

A subject method involves use of an ALDH agonist (also referred to as "ALDH activator"). A suitable ALDH agonist increases an enzymatic activity of an ALDHa, ALDH3, or ALDH6 polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH polypeptide in the absence of the agonist.

In some embodiments, a suitable ALDH agonist increases an enzymatic activity (e.g., an aldehyde dehydrogenase activity, a reductase activity, or an esterase activity) of an ALDH1 polypeptide comprising an amino acid sequence set forth in FIG. 5A or 5B, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH1 polypeptide in the absence of the agonist.

In some embodiments, a suitable ALDH agonist increases an enzymatic activity (e.g., an aldehyde dehydrogenase activity, a reductase activity, or an esterase activity) of an ALDH3 polypeptide comprising an amino acid sequence set forth in FIG. 6, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH3 polypeptide in the absence of the agonist.

In some embodiments, a suitable ALDH agonist increases an enzymatic activity (e.g., an aldehyde dehydrogenase activity, a reductase activity, or an esterase activity) of an ALDH6 polypeptide comprising an amino acid sequence set forth in FIG. 7A, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH6 polypeptide in the absence of the agonist.

In some embodiments, a suitable ALDH agonist has an $EC_{50}$ (half maximal effective concentration) of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM from about 1 μM to about 10 μM from about 10 μM to about 25 μM from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM.

In some embodiments, a suitable ALDH agonist is a compound of generic Formula I, as shown below:

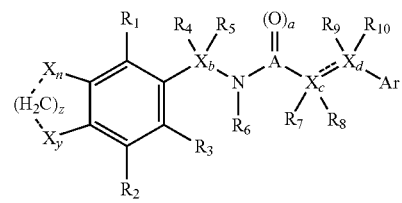

Formula I where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond; where z is the integer 0, 1, or 2;

where — is an optional double bond;

where each of $R_1$, $R_2$, $R_3$, $R_4$, $R_5$, $R_6$, $R_7$, $R_8$, $R_9$, and $R_{10}$ is independently selected from H; C; N; O; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where A is C or S; and where a=1 when A=C; and where a=2 when A=S;

where $X_b$ is C, N, O, or S; where b is the integer 0 or 1;
where $X_c$ is C, N, O, or S; where c is the integer 0 or 1;
where $X_d$ is C, N, O, or S; where d is the integer 0 or 1; and where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

For example, in some embodiments, Ar of Formula I is:

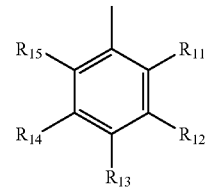

where $R_{11}$-$R_{15}$ are each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group. In some embodiments, Ar of Formula I is a substituted naphthalene group, e.g., a methoxy-substituted naphthalene group.

In other embodiments, Ar of Formula I is a substituted or unsubstituted heterocyclic group, e.g., a substituted or unsubstituted pyridine, a substituted or unsubstituted pyrazine, a substituted or unsubstituted pyrimidine, a substituted or unsubstituted pyridazine, a substituted or unsubstituted pyrrole, a substituted or unsubstituted furan, a substituted or unsubstituted pyrazole, a substituted or unsubstituted oxazole, a substituted or unsubstituted isoxazole, a substituted or unsubstituted thiazole, a substituted or unsubstituted imidazole, a substituted or unsubstituted thiophene, a substituted or unsubstituted quinoline, or a substituted or unsubstituted isoquinoline group. In some embodiments, Ar of Formula I is a substituted thiophene group, e.g., a 2-carboxylic acid amide-substituted thiophene group.

In other embodiments, Ar of Formula I is a substituted or unsubstituted heterocyclic group, e.g., a substituted or unsubstituted pyridine, a thiazole, an imidazole, a thiophene, a quinoline, an isoquinoline, or a furan group. In some embodiments, Ar of formula I is a substituted pyridine-oxide.

In some embodiments, a suitable ALDH agonist has the structure of Compound Alda-52, as shown below:

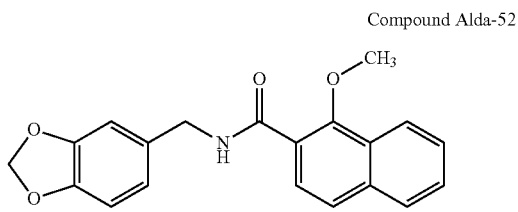 [SMILES: COc1c(C(=O)NCc2ccc3c(c2)OCO3)ccc2ccccc12]

Compound Alda-52

Compound Alda-52: 1-methoxy-naphthalene-2-carboxylic acid (benzo[1,3]dioxol-5-ylmethyl)-amide.

In some embodiments, a suitable ALDH agonist has the structure of Compound Alda-84, as shown below:

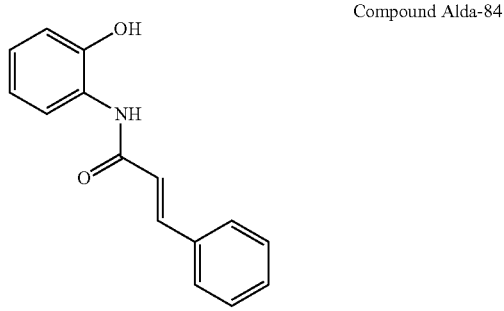 [SMILES: O=C(/C=C/c1ccccc1)Nc1ccccc1O]

Compound Alda-84

Compound Alda-84: N-(2-hydroxy-phenyl)-3-phenyl-acrylamide.

In some embodiments, a suitable ALDH agonist is a compound of generic Formula Ia, as shown below:

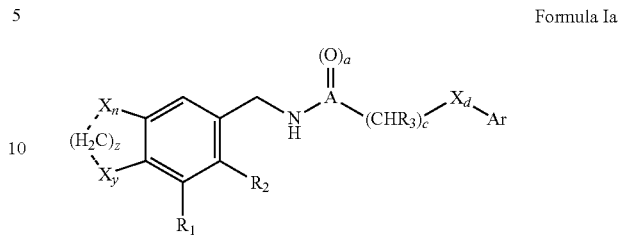

Formula Ia where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where A=C or S, and where a=1 when A=C; and where a=2 when A=S;

where $R_1$, $R_2$, and $R_3$ are each independently selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where c is the integer 0 or 1;

where $X_d$ is C, N, O, or S; where d is the integer 0 or 1; and where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, a suitable ALDH agonist is a compound of sub-generic Formula Ib, as shown below:

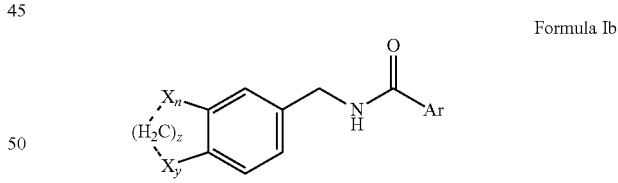

Formula Ib where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, is not a bond, and one or more oxygen atoms (X) are present, oxygen is attached to a methyl group;

where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, a suitable ALDH agonist is a compound of sub-generic Formula Ic, as shown below:

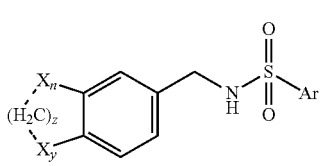

Formula Ic where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, a suitable ALDH agonist is a compound of sub-generic Formula Id, as shown below:

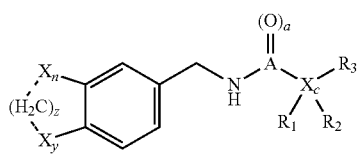

Formula Id where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where A=C or S, and where a=1 when A=C; and where a=2 when A=S;

where $X_c$ is C, N, O, or S; where c is the integer 0 or 1; and where $R_1$ and $R_2$ are each independently selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $R_3$ is selected from a substituted polycyclic group, an unsubstituted polycyclic group, a substituted hetero polycyclic group, and an unsubstituted hetero polycyclic group;

or a pro-drug, a pharmaceutically acceptable salt, an analog, or a derivative thereof.

In some embodiments, a suitable ALDH agonist is a compound of sub-generic Formula Ie, as shown below:

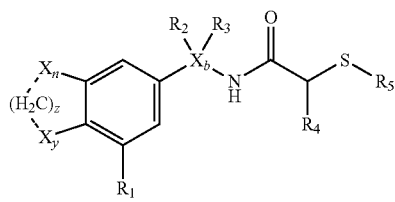

Formula Ie where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where $X_b$ is C, N, O, or S; where c is the integer 0 or 1; and where $R_1$, $R_2$, $R_3$ and $R_4$ are each independently selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $R_5$ is selected from a substituted polycyclic group, an unsubstituted polycyclic group, a substituted hetero polycyclic group, and an unsubstituted hetero polycyclic group;

or a pro-drug, a pharmaceutically acceptable salt, an analog, or a derivative thereof.

In some embodiments, a suitable ALDH agonist is a compound of generic Formula If, as shown below:

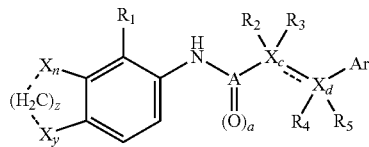

Formula If where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where — is an optional double bond;

where A=C or S, and where a=1 when A=C; and where a=2 when A=S;

where $R_1$, $R_2$, $R_3$, $R_4$ and $R_5$ are each independently selected from H; —OH; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $X_c$ is C, N, O, or S; where c is the integer 0 or 1;

where $X_d$ is C, N, O, or S; where c is the integer 0 or 1; and where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

An exemplary, non-limiting compound of Formula If is Alda-84.

In some embodiments, a suitable ALDH agonist is a compound of generic Formula II, as shown below:

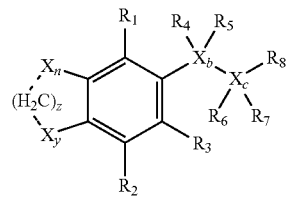

Formula II where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond; where z is the integer 0, 1, or 2;

where $R_1$ to $R_7$ is each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where $X_b$ is C, N, O, or S; where b is the integer 0 or 1;

where $X_c$ is C, N, O, or S; where c is the integer 0 or 1; and where $R_8$ is selected from a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

For example, in some embodiments, $R_8$ of Formula II is a substituted or unsubstituted heterocyclic group, e.g., a substituted or unsubstituted pyridine, a substituted or unsubstituted pyrazine, a substituted or unsubstituted pyrimidine, a substituted or unsubstituted pyridazine, a substituted or unsubstituted pyrrole, a substituted or unsubstituted furan, a substituted or unsubstituted pyrazole, a substituted or unsubstituted oxazole, a substituted or unsubstituted isoxazole, a substituted or unsubstituted thiazole, a substituted or unsubstituted imidazole, a substituted or unsubstituted thiophene, a substituted or unsubstituted quinoline, or a substituted or unsubstituted isoquinoline group. In some embodiments, $R_8$ of Formula II is a substituted pyrrolidin-2-one group, a substituted pyrrolo[2,3-d]pyrimidine group, a substituted pyrazolo[3,4-d]pyrimidine group, a substituted pyrazin-2-one group, or a substituted 4,5,6,7-tetrahydro-tetrazolo[1,5-a]pyrimidine group.

In other embodiments, $R_8$ of Formula II is a substituted or unsubstituted heterocyclic group, e.g., a substituted or unsubstituted pyridine, a thiazole, an imidazole, a thiophene, a quinoline, an isoquinoline, or a furan group. In some embodiments, $R_8$ of Formula II is a substituted pyridine-oxide.

In some embodiments, a suitable ALDH agonist has the structure of Compound Alda-83, as shown below:

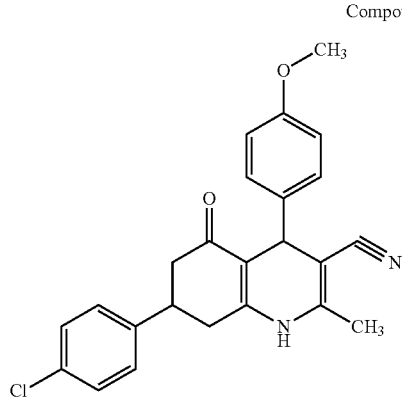

Compound Alda-83

Compound Alda-83: 7-(4-chloro-phenyl)-4-(4-methoxy-phenyl)-2-methyl-5-oxo-1,4,5,6,7,8-hexahydro-quinoline-3-carbonitrile.

In some embodiments, a suitable ALDH agonist has the structure of sesamin, as shown below:

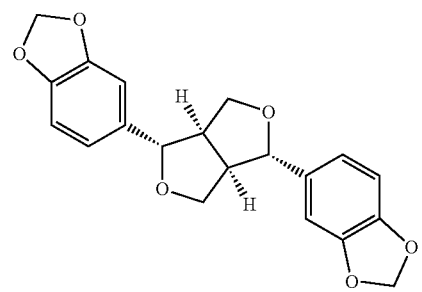

Sesamin

Sesamin is 5,5'-(1S,3aR,4S,6aR)-tetrahydro-1H,3H-furo[3,4-c]furan-1,4-diylbis(1,3-benzodioxole).

In some embodiments, a suitable ALDH agonist has the structure of isosafrole, as shown below:

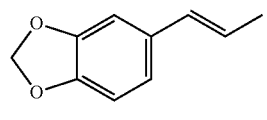

Isosafrole

Isosafrole is 5-propenyl-benzo[1,3]dioxole.

In some embodiments, a suitable ALDH agonist has the structure of Alda-89, as shown below:

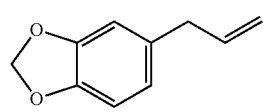

Alda-89 is 5-(2-propenyl)-1,3-benzodioxole.

In some embodiments, a suitable ALDH agonist is a compound of sub-generic Formula IIa, as shown below:

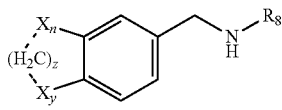

Formula IIa where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where $R_8$ is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, a suitable ALDH agonist is a compound of sub-generic Formula IIb, as shown below:

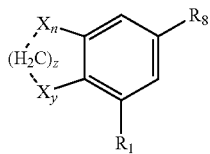

Formula IIb where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where $R_1$ is selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $R_8$ is selected from a substituted cyclic group, an unsubstituted cyclic group, a substituted heterocyclic group, and an unsubstituted heterocyclic group;

or a pro-drug, a pharmaceutically acceptable salt, an analog, or a derivative thereof.

In some embodiments, a suitable ALDH agonist is a compound of sub-generic Formula IIc, as shown below:

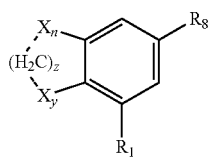

Formula IIc where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where $R_1$ is selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $R_8$ is selected from a substituted bicyclic group, an unsubstituted bicyclic group, a substituted hetero bicyclic group, and an unsubstituted hetero bicyclic group;

or a pro-drug, a pharmaceutically acceptable salt, an analog, or a derivative thereof.

In some embodiments, a suitable ALDH agonist is a compound of sub-generic Formula IId, as shown below:

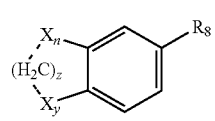

Formula IId where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where $R_8$ is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, a suitable ALDH agonist is a compound of generic Formula III, as shown below:

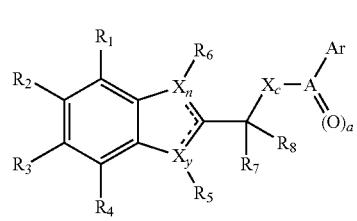

Formula III where $X_n$ and $X_y$ are each independently C, N, O, or S; where n is the integer 0, 1 or 2; where y is the integer 0, 1 or 2;

where — is an optional double bond;

where each of $R_1$, $R_2$, $R_3$, $R_4$, $R_5$, $R_6$, $R_7$ and $R_8$ is independently selected from H; C; N; O; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where A is C or S; and where a=1 when A=C; and where a=2 when A=S;

where $X_c$ is C, N, O, or S; where c is the integer 0 or 1;

where Ar is selected from a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

For example, in some embodiments, Ar of Formula III is a substituted or unsubstituted heterocyclic group, e.g., a substituted or unsubstituted pyridine, a substituted or unsubstituted pyrazine, a substituted or unsubstituted pyrimidine, a substituted or unsubstituted pyridazine, a substituted or unsubstituted pyrrole, a substituted or unsubstituted furan, a substituted or unsubstituted pyrazole, a substituted or unsubstituted oxazole, a substituted or unsubstituted isoxazole, a substituted or unsubstituted thiazole, a substituted or unsubstituted imidazole, a substituted or unsubstituted thiophene, a substituted or unsubstituted quinoline, or a substituted or unsubstituted isoquinoline group.

In some embodiments, a suitable ALDH agonist has the structure of Compound Alda-81, as shown below:

Compound Alda-81

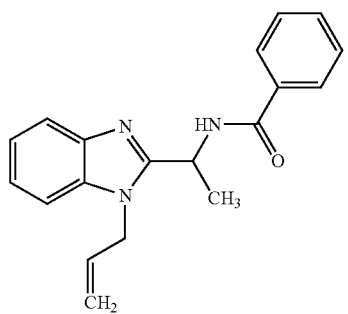

Compound Alda-81: N-[1-(1-allyl-1H-benzoimidazol-2-yl)-ethyl]-benzamide.

In some embodiments, a suitable ALDH agonist is a compound of generic Formula IV, as shown below:

Formula IV

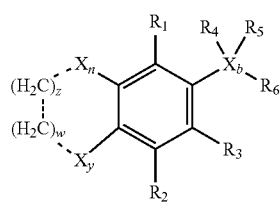

where $X_n$ and $X_y$ are each independently C, N, O, or S; where n is the integer 0, 1 or 2; where y is the integer 0, 1 or 2;

where . . . (dotted line) is an optional bond;

where z is the integer 0 or 1, with the provisos that: 1) z=0 when X=halogen and . . . is not a bond; and 2) when z=0, X=O, . . . is not a bond, and one or more oxygen atoms (X) are present, oxygen is attached to a methyl group;

where w is the integer 0 or 1, with the provisos that: 1) w=0 when X=halogen and . . . is not a bond; and 2) when w=0, X=O, . . . is not a bond, and one or more oxygen atoms (X) are present, oxygen is attached to a methyl group;

where each of $R_1$, $R_2$, $R_3$, $R_4$, and $R_5$ is independently selected from H; C; N; O; a halo (e.g., bromo, fluoro, chloro, iodo); a substituted or unsubstituted alkoxyl group, a substituted or unsubstituted amine group, a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where $X_b$ is C, N, O, or S; where b is the integer 0 or 1;

where $R_6$ is selected from a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

For example, in some embodiments, $R_6$ of Formula IV is a substituted or unsubstituted alkenyl group, e.g., a substituted or unsubstituted ethenyl group, a substituted or unsubstituted propenyl group, a substituted or unsubstituted allyl group, and the like.

In some embodiments, a suitable ALDH agonist is a compound of generic Formula V, as shown below:

Formula V

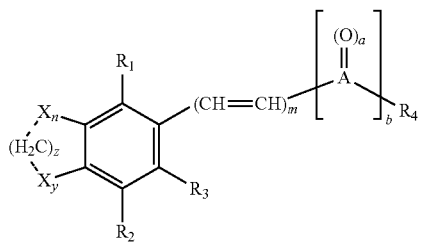

where $X_n$ and $X_y$ are each independently C, N, O, or S; where n is the integer 0, 1 or 2; where y is the integer 0, 1 or 2;

where . . . (dotted line) is an optional bond;

where z is the integer 0 or 1, with the provisos that: 1) z=0 when X=halogen and . . . is not a bond; and 2) when z=0, X=O, . . . is not a bond, and one or more oxygen atoms (X) are present, oxygen is attached to a methyl group;

where each of $R_1$, $R_2$ and $R_3$ is independently selected from H; C; N; O; a halo (e.g., bromo, fluoro, chloro, iodo); a substituted or unsubstituted alkoxyl group, a substituted or unsubstituted amine group, a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where m is an integer from 1 to 10;

where A is C or S; and where a=1 when A=C; and where a=2 when A=S;

where b is the integer 0 or 1;

where $R_4$ is selected from a hydroxyl group, an amine group, a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

For example, in some embodiments, $R_4$ of Formula V is a substituted or unsubstituted heterocyclic group, e.g., a substituted or unsubstituted piperidine, a substituted or unsubstituted pyran, a substituted or unsubstituted pyranone, a substituted or unsubstituted pyridine, a substituted or unsubstituted pyrazine, a substituted or unsubstituted pyrimidine, a substituted or unsubstituted pyridazine, a substituted or unsubstituted pyrrole, a substituted or unsubstituted furan, a substituted or unsubstituted pyrazole, a substituted or unsubstituted oxazole, a substituted or unsubstituted isoxazole, a substituted or unsubstituted thiazole, a substituted or unsubstituted imidazole, a substituted or unsubstituted thiophene, a substituted or unsubstituted quinoline, or a substituted or unsubstituted isoquinoline group.

In some embodiments, a suitable ALDH agonist has the structure of piperine, as shown below:

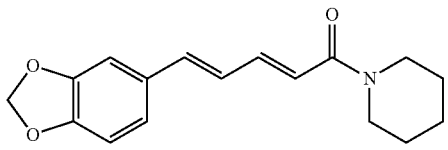

Piperine

Piperine is 1-[5-(1,3-benzodioxol-5-yl)-1-oxo-2,4-pentadienyl]piperidine.

In some embodiments, a suitable ALDH agonist has the structure of methysticin, as shown below:

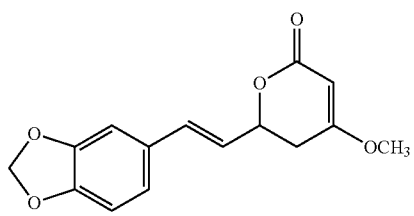

Methysticin

Methysticin is 6-(2-Benzo[1,3]dioxol-5-yl-vinyl)-4-methoxy-5,6-dihydro-pyran-2-one.

In some embodiments, a suitable ALDH agonist is a compound of generic Formula Va, as shown below:

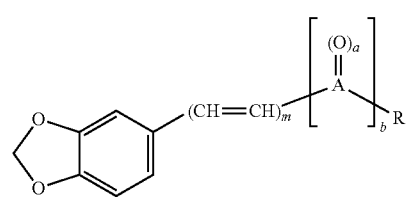

Formula Va where m is an integer from 1 to 10;

where A is C or S; and where a=1 when A=C; and where a=2 when A=S;

where b is the integer 0 or 1;

where R is selected from a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

In some embodiments, a suitable ALDH agonist is a compound of generic Formula A, as shown below:

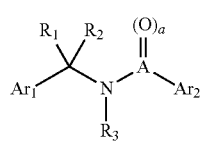

Formula A where each of $R_1$, $R_2$, and $R_3$ is independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where A is C or S and where a=1 when A=C; and where a=2 when A=S; and where $Ar_1$ and $Ar_2$ are independently selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

For example, in some embodiments, $Ar_1$ of Formula A are independently:

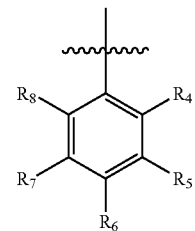

where $R_4$-$R_8$ are each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group. In other embodiments, $Ar_1$ of Formula A are independently a substituted or unsubstituted heterocyclic group, e.g., a substituted or unsubstituted pyridine, a thiazole, an imidazole, a thiophene, a quinoline, an isoquinoline, or a furan group.

In exemplary embodiments of Formula A, $Ar_2$ of Formula A is independently a substituted pyridine oxide. For example, in exemplary embodiments of Formula A, $Ar_2$ of Formula A is independently a substituted pyridine oxide selected from the formulas,

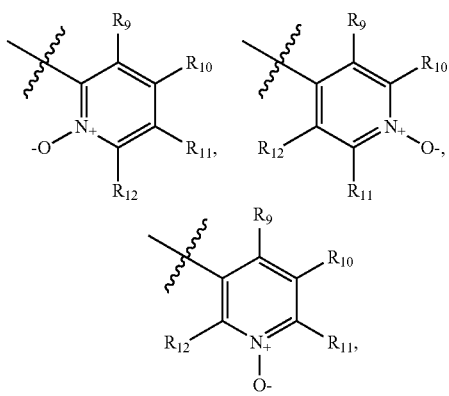

where $R_9$ to $R_{12}$ is each independently selected from H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group.

In some embodiments, a suitable ALDH agonist is a compound of generic Formula B, as shown below:

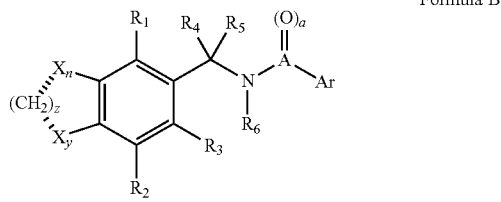
Formula B where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond; where z is the integer 0, 1, or 2;

where A is C or S, and where a=1 when A=C; and where a=2 when A=S;

where Ar is an unsubstituted or substituted aryl group, a substituted heteroaryl group, or an unsubstituted heteroaryl group; and where $R_1$ to $R_6$ is each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

or a pro-drug, a pharmaceutically acceptable salt, an analog, or a derivative thereof.

In exemplary embodiments of Formula B, Ar is independently a substituted pyridine oxide. For example, in exemplary embodiments of Formula B, Ar is independently a substituted pyridine oxide selected from a formula shown below,

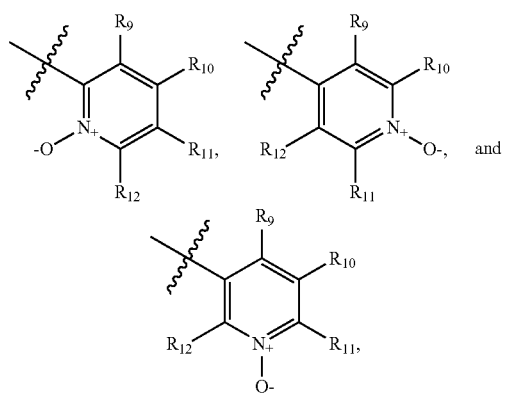

where $R_9$ to $R_{12}$ is each independently selected from a group including, but not limited to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group.

In some embodiments, a suitable ALDH agonist is a compound of generic formula Ia, as shown below:

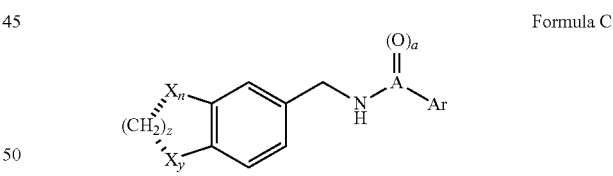
Formula C where $X_n$ and $X_y$ are each independently H, C, N, O, or a halogen (e.g., F, Br, Cl, or I);

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where n is the integer 0 or 1;

where y is the integer 0 or 1;

where A=C or S, and where a=1 when A=C; and where a=2 when A=S;

where Ar is independently a substituted pyridine oxide selected the formula from below,

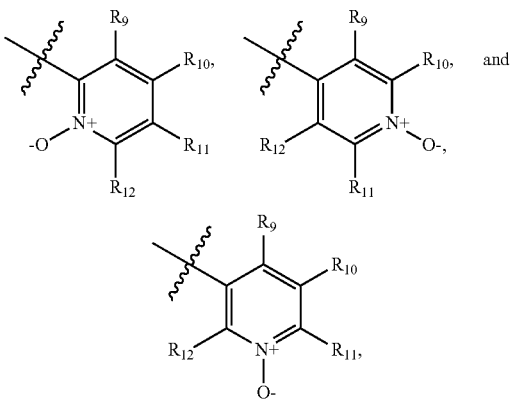

where $R_9$ to $R_{12}$ is each independently selected from a group including, but not limit to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group;

or a pro-drug, a pharmaceutically acceptable salt, an analog, or a derivative thereof.

In some embodiments, a suitable ALDH agonist is capsaicin. Capsaicin has the structure:

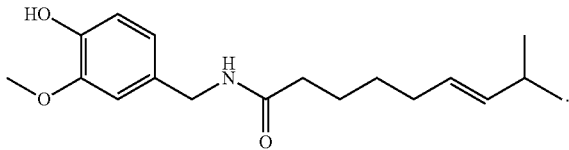 [SMILES: COc1cc(CNC(=O)CCCC/C=C/C(C)C)ccc1O]

In some embodiments, a suitable ALDH agonist has the structure of Formula D, as shown below.

Formula D

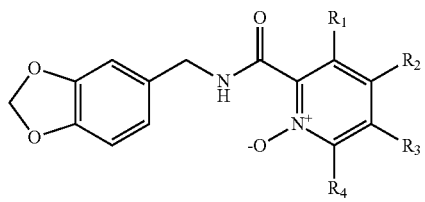

where $R_1$ to $R_4$ is each independently selected from, but not limited to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester or an amide group;

or a pro-drug, a pharmaceutically acceptable salt, an analog, or a derivative thereof.

In some embodiments, a suitable ALDH agonist has the structure of Formula E, as shown below.

Formula E

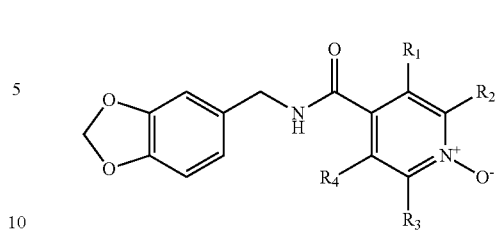

where $R_1$ to $R_4$ is each independently selected from, but not limit to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group;

or a pro-drug, a pharmaceutically acceptable salt, an analog, or a derivative thereof.

In some embodiments, a suitable ALDH agonist has the structure of Formula c, as shown below.

Formula F

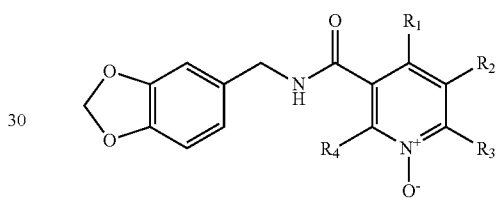

where $R_1$ to $R_4$ is each independently selected from such group, but not limit to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group;

or a pro-drug, a pharmaceutically acceptable salt, an analog, or a derivative thereof.

Whether a compound is an ALDH agonist can be readily ascertained. Assays for dehydrogenase activity of ALDH are known in the art, and any known assay can be used. Examples of dehydrogenase assays are found in various publications, including, e.g., Sheikh et al. ((1997) *J. Biol. Chem.* 272:18817-18822); Vallari and Pietruszko (1984) *J. Biol. Chem.* 259:4922; and Farres et al. ((1994) *J. Biol. Chem.* 269:13854-13860).

Figure 4:
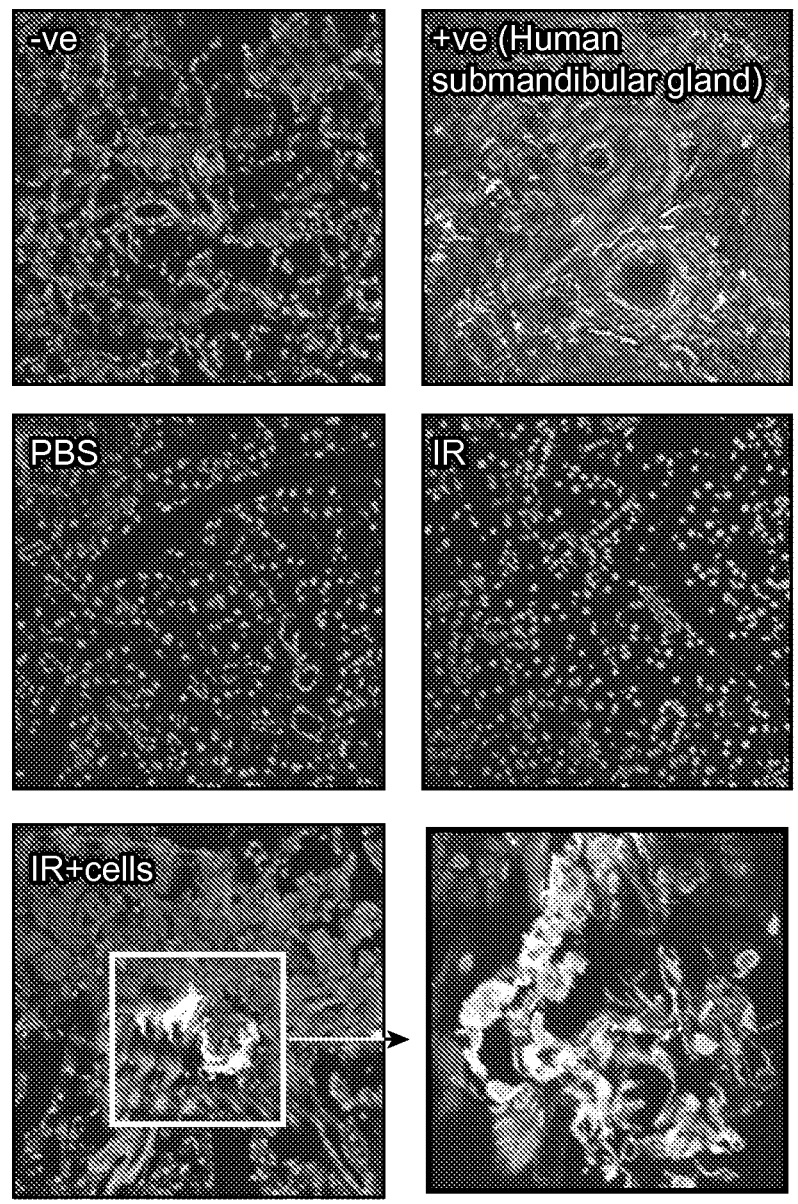
FIG. 4 shows the results of implantation of human salivary cells into the submandibular gland of an irradiated nude mouse.

As an example of an assay for dehydrogenase activity, ALDH aldehyde dehydrogenase activity is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and an aldehyde substrate such as 14 μM propionaldehyde. Reduction of $NAD^+$ is monitored at 340 nm using a spectrophotometer, or by fluorescence increase using a fluoromicrophotometer Enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as described in US 2005/0171043; and WO 2005/057213, and as depicted schematically in FIG. 4. In an exemplary assay, the reaction is carried out at 25° C. in 0.1 sodium pyrophosphate (NaPPi) buffer, pH 9.0, 2.4 mM $NAD^+$ and 10 mM acetaldehyde as the substrate. Enzymatic activity is measured by a reductive reaction of $NAD^+$ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213. Detection of fluorescent resorufin at 590 nm provides amplified and more sensitive signals for any change in ALDH aldehyde dehydrogenase enzymatic activity. $NADP^+$ can be used in place of $NAD^+$ in this assay. In some embodiments, a substrate other than the substrate depicted in FIG. 4 is used. Suitable substrates include, but are not limited to, octylaldehyde, phenylacetaldehyde, retinaldehyde, and 4-hydroxynonenal.

As another example, the effect of a compound on aldehyde dehydrogenase activity of an ALDH polypeptide can be assayed as described in Wierzchowski et al. ((1996) *Analytica Chimica Acta* 319:209), in which a fluorogenic synthetic substrate, e.g., 7-methoxy-1-naphthaldehyde is used. For example, the reaction could include 7-methoxy-1-naphthaldehyde, $NAD^+$, an ALDH polypeptide, and an ALDH agonist to be tested; fluorescence (excitation, 330 nm; emission 390 nm) is measured as a readout of enzymatic activity.

Whether a compound increases an esterase activity of an ALDH polypeptide can be determined using any known assay for esterase activity. For example, esterase activity of ALDH can be determined by monitoring the rate of p-nitrophenol formation at 400 nm in 25 mM N,N-Bis(2-hydroxyethyl)-2-amino ethanesulfonic acid (BES) (pH 7.5) with 800 µM p-nitrophenyl acetate as the substrate at room temperature in the absence or presence of added $NAD^+$. A pH-dependent molar extinction coefficient of 16 $mM^{-1}$ $cm^{-1}$ at 400 nm for nitrophenol can be used. See, e.g., Larson et al. (2007) *J. Biol. Chem.* 282:12940). Esterase activity of an ALDH polypeptide can be determined by measuring the rate of p-nitrophenol formation at 400 nm in 50 mM Pipes (pH 7.4) with 1 mM p-nitrophenylacetate as the substrate. A molar extinction coefficient of $18.3 \times 10^3$ $M^{-1}$ $cm^{-1}$ at 400 nm for p-nitrophenolate can be used for calculating its rate of formation. See, e.g., Ho et al. (2005) *Biochemistry* 44:8022).

Whether a compound increases a reductase activity of ALDH can be determined using any known assay for reductase activity. A reductase activity of ALDH can be determined by measuring the rate of 1,2-glyceryl dinitrate and 1,3-glyceryl dinitrate formation using a thin layer chromatography (TLC) or liquid scintillation spectrometry method, using a radioactively labeled substrate. For example, 0.1 mM or 1 mM GTN (glyceryl trinitrate) is incubated with the assay mixture (1 ml) containing 100 mM KPi (pH 7.5), 0.5 mM EDTA, 1 mM NADH, 1 mM NADPH in the presence the ALDH. After incubation at 37° C. for about 10 minutes to about 30 minutes, the reaction is stopped and GTN and its metabolites are extracted with 3×4 ml ether and pooled, and the solvent is evaporated by a stream of nitrogen. The final volume is kept to less than 100 µl in ethanol for subsequent TLC separation and scintillation counting. See, e.g., Zhang and Stamler (2002) *Proc. Natl. Acad. Sci. USA* 99:8306.

As noted above, in some embodiments, a suitable ALDH agonist is pure, e.g., at least 80%, at least about 90% pure, at least about 98% pure, or at least about 99% pure, by weight.

Natural Extracts

The present disclosure also provides for use of ALDH agonists in natural extracts, e.g., extracts of plants and other organisms that naturally contain an ALDH agonist. Natural formulations and extracts can comprise an ALDH agonist in an amount by weight of from about 0.01% to about 30%, or from about 30% to about 80%, e.g., from about 0.01% to about 0.05%, from about 0.05% to about 0.1%, from about 0.1% to about 0.5%, from about 0.5% to about 1%, from about 1% to about 2.5%, from about 2.5% to about 5%, from about 5% to about 7.5%, from about 7.5% to about 10%, from about 10% to about 12.5%, from about 12.5% to about 15%, from about 15% to about 20%, from about 20% to about 25%, or from about 25% to about 30%. In some embodiments, a suitable natural formulation or natural extract comprises an ALDH agonist in an amount by weight of from about 30% to about 35%, from about 35% to about 40%, from about 40% to about 45%, from about 45% to about 50%, from about 50% to about 60%, from about 60% to about 70%, or from about 70% to about 80%. As used herein, a "natural formulation" or a "natural extract" can include components of a plant or other natural source of an ALDH agonist, but does not exclude inclusion of components not normally found in a plant source of an ALDH agonist, e.g., the "natural formulation" or "natural extract" can include added components not normally found in a plant source or other natural source of an ALDH agonist.

A plant or plant part can be extracted either singly or sequentially with one or more of an aqueous solution, an alcohol, a polar organic solvent, and a non-polar organic solvent. In some embodiments, an ALDH agonist is water soluble (hydrophilic) and is present in an aqueous phase of a natural extract. For example, in some embodiments, a plant or plant part is extracted with 100% water. In other embodiments, an ALDH agonist is hydrophobic and is present in an organic phase of a natural extract. For example, a plant or a plant part can be extracted with an organic solvent such as ethyl acetate or methylene chloride. In some embodiments, the plant or plant part is extracted with alcohol, e.g., methanol or butanol. In some embodiments, the plant or plant part is extracted with methanol:chloroform (1:1 vol:vol). In some embodiments, the plant or plant part is extracted with methanol:water from 95:5 to 1:1. In some embodiments, the plant or plant part is extracted sequentially with an alcohol, then with an alcohol:chloroform mixture. Polar organic solvents include, e.g., tetrahydrofuran, acetonitrile, acetone, and isopropyl alcohol. In some embodiments, the plant or plant part is extracted with a polar organic solvent. Extraction methods are known in the art, and are described in, e.g., U.S. Pat. Nos. 7,282,150 and 7,172,772.

The natural extract can be obtained by extracting a plant or plant part at a temperature of from about 15° C. to about 20° C., from about 20° C. to about 25° C., from about 25° C. to about 30° C., from about 30° C. to about 35° C., from about 35° C. to about 40° C., from about 40° C. to about 45° C., from about 45° C. to about 50° C., from about 50° C. to about 60° C., from about 60° C. to about 70° C., from about 70° C. to about 80° C., from about 80° C. to about 90° C., or from about 90° C. to about 100° C.

A natural extract includes an extract of a whole plant or one or more parts of a plant, where plant parts include leaves, stems, rhizomes, roots, tubers, bulbs, flowers, bark, seeds, fruit, and the like. Thus, sources of an ALDH agonist include, e.g., whole plant or one or more parts of a plant, where plant parts include leaves, stems, rhizomes, tubers, bulbs, roots, flowers, bark, seeds, fruit, and the like. Prior to extraction, the plant or plant part can be subjected to one or more processing steps; e.g., prior to extraction, the plant or plant part can be dried, powdered, frozen, steamed, ground, pulverized, or fermented. Pulverizing can be achieved by carrying out one or more of homogenizing, milling, grinding, chopping, blending, cutting, and tearing.

Combinations of two or more extracts are also contemplated, e.g., extracts of two or more different plant parts from the same plant; extracts from two or more plants of the same genus, where the plants are of two or more different species; extracts from two or more plants of two or more different genuses; a combination of an aqueous extract and an alcohol extract; a combination of an aqueous extract and a polar organic solvent extract; a combination of an aqueous extract and a non-polar organic solvent extract; etc.

A suitable natural extract can be formulated in any form convenient for use, e.g., a lozenge, a capsule, a powder, a liquid solution, a gel, etc. Any of a variety of components can be added to a natural extract, including, e.g., fillers, binders, sweeteners, flavors and other ingredients. Nearly any excipients that are known for use in the preparation of oral dosage pharmaceutical products, or natural supplement products, can be used. Examples of such excipients include without limitation, carbomer, carboxymethylcellulose sodium, cellulose, dextrin, dextrose, ethylcellulose, fructose, gelatin, guar gum, hydroxyethyl cellulose, hydroxypropyl cellulose, hydroxypropyl methylcellulose, glucose, maltodextrin, mannitol, methylcellulose, microcrystalline cellulose, polymethacrylates, povidone, sorbitol, starches, sucrose, sugar, sucralose, stevia, and flavor agents.

Pharmaceutical Compositions, Dosages, Routes of Administration

In some instances, as discussed above, an ALDH agonist (e.g., an ALDH1 agonist and/or an ALDH3 agonist and/or an ALDH6 agonist) can be used to increase the number of adult salivary stem cells in vivo, e.g., an effective amount of an ALDH agonist is administered to an individual in need thereof. The terms "ALDH agonist" and "ALDH activator" are also referred to herein as "active agent." For administration to an individual, a suitable ALDH agonist is formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds. $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The term "unit dosage form," as used herein, refers to physically discrete units suitable as unitary dosages for human and animal subjects, each unit containing a predetermined quantity of an active agent (e.g., an ALDH agonist) calculated in an amount sufficient to produce the desired effect in association with a pharmaceutically acceptable diluent, carrier or vehicle. The specifications for an active agent depend on the particular compound employed and the effect to be achieved, and the pharmacodynamics associated with each compound in the host.

In the subject methods, a suitable ALDH agonist may be administered to the host using any convenient means capable of resulting in the desired outcome, e.g., reduction of disease, reduction of a symptom of a disease, etc. Thus, a suitable ALDH agonist can be incorporated into a variety of formulations for therapeutic administration. More particularly, a suitable ALDH agonist can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

In pharmaceutical dosage forms, a suitable ALDH agonist ("active agent") may be administered in the form of its pharmaceutically acceptable salts, or an active agent may be used alone or in appropriate association, as well as in combination, with other pharmaceutically active compounds. The following methods and excipients are merely exemplary and are in no way limiting.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. An active agent can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycol monomethyl ethers, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the active agent. Similarly, unit dosage forms for injection or intravenous administration may comprise an active agent in a composition as a solution in sterile water, normal saline or another pharmaceutically acceptable carrier.

An active agent can be formulated for administration by injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Dosages and Dosing

Depending on the subject and condition being treated and on the administration route, an active agent may be administered in dosages of, for example, 0.1 µg to 500 mg/kg body weight per day, e.g., from about 0.1 µg/kg body weight per day to about 1 µg/kg body weight per day, from about 1 µg/kg body weight per day to about 25 µg/kg body weight per day, from about 25 µg/kg body weight per day to about 50 µg/kg body weight per day, from about 50 µg/kg body weight per day to about 100 µg/kg body weight per day, from about 100 µg/kg body weight per day to about 500 µg/kg body weight per day, from about 500 µg/kg body weight per day to about 1 mg/kg body weight per day, from about 1 mg/kg body weight per day to about 25 mg/kg body weight per day, from about 25 mg/kg body weight per day to about 50 mg/kg body weight per day, from about 50 mg/kg body weight per day to about 100 mg/kg body weight per day, from about 100 mg/kg body weight per day to about 250 mg/kg body weight per day, or from about 250 mg/kg body weight per day to about 500 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

For example, an ALDH1 activator, and/or an ALDH3 activator, and/or ALDH6 activator can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

An exemplary dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is in some embodiments one which provides up to about 1 µg to about 1,000 µg or about 10,000 µg of an active agent in a blood sample taken from the individual being treated, about 24 hours after administration of the compound to the individual.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound(s) in a composition as a solution in sterile water, normal saline or another pharmaceutically acceptable carrier.

In some embodiments, multiple doses of an active agent are administered. The frequency of administration of a compound ("active agent") can vary depending on any of a variety of factors, e.g., severity of the symptoms, etc. For example, in some embodiments, an active agent is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in some embodiments, an active agent is administered continuously.

The duration of administration of an active agent, e.g., the period of time over which an active agent is administered, can vary, depending on any of a variety of factors, e.g., patient response, etc. For example, an active agent can be administered over a period of time ranging from about one day to about one week, from about two weeks to about four weeks, from about one month to about two months, or from about two months to about four months, or more.

Routes of Administration

A suitable ALDH agonist is administered to an individual using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g., administration for longer than one week, e.g., administration over a period of time of from about 2 weeks to about one month, from about one month to about 3 months, from about 3 months to about 6 months, or more).

Conventional and pharmaceutically acceptable routes of administration include intranasal, intramuscular, intratracheal, subcutaneous, intradermal, transdermal, sublingual, topical application, intravenous, ocular (e.g., topically to the eye, intravitreal, etc.), rectal, nasal, oral, and other enteral and parenteral routes of administration. Routes of administration may be combined, if desired, or adjusted depending upon the agent and/or the desired effect. The compound can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, ocular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of a suitable ALDH agonist through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Treatment Methods

The present disclosure provides various treatment methods, generally involving administering to an individual in need thereof an effective amount of an ALDH agonist and/or an expanded population of adult salivary stem cells (e.g., salivary stem cells expanded in vitro or ex vivo by contacting the salivary stem cells with an ALDH agonist).

Local and/or Systemic ALDH Agonist Administration

As noted above, individuals with head and neck cancer commonly undergo radiotherapy (RT) which often results in permanent damage to the salivary glands, causing loss of function and subsequent RT-related xerostomia or dry mouth. Treatment methods of the present disclosure may include in vivo activation of one or more ALDH enzymes (e.g., ALDH1, ALDH3 and/or ALDH6, etc.) in tissues of the head and neck region (one or more salivary glands, for example) of an individual with head and neck cancer who will undergo, or has undergone, radiotherapy to treat the head and neck cancer. The methods may include administering an ALDH agonist systemically (e.g., by oral, intravenous, or other systemic administration) or locally (e.g., by local injection and/or topical application at a target site of a composition that includes a modulator of ALDH activity). According to one embodiment of the present disclosure, the ALDH agonist may be administered (e.g., systemically and/or locally) before the individual with head and neck cancer undergoes radiation therapy. In another embodiment, the ALDH agonist may be administered (e.g., systemically and/or locally) after the individual with head and neck cancer undergoes radiation therapy. In yet another embodiment, the ALDH agonist is administered before and after the individual undergoes radiation therapy.

As noted above, in some embodiments, an ALDH agonist (e.g., an activator of ALDH1, ALDH3, ALDH6, or a combination thereof) is administered as a "pretreatment" to an individual before the individual undergoes radiation treatment, e.g., from about 1 hour to about 1 week before the radiation treatment, e.g., from about 1 hour to about 2 hours, from about 2 hours to about 4 hours, from about 4 hours to about 8 hours, from about 8 hours to about 12 hours, from about 12 hours to about 16 hours, from about 16 hours to about 24 hours, from about 24 hours to about 36 hours, from about 36 hours to about 48 hours, from about 48 hours to about 72 hours, or from about 72 hours to about 1 week preceding the radiation treatment.

Pretreatment with an ALDH agonist (e.g., an ALDH1, ALDH3 or ALDH6 agonist; or a combination of two or more of such agonists) is useful, for example, to expand the number of adult salivary stem cells in vivo, such that the probability of a sufficient number of stem cells surviving the radiation treatment is increased. The above situation is only one example of a circumstance when a subject would benefit from pretreatment with a suitable ALDH agonist.

In some embodiments, a suitable ALDH agonist is administered after radiation therapy. For example, a suitable ALDH agonist administered after radiation treatment is effective for mitigating the adverse effects of the radiation treatment on the salivary gland and corresponding salivary function. In some embodiments, a suitable ALDH agonist is administered within 1 minute to within 15 hours, e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 60 minutes to about 2 hours, from about 2 hours to about 4 hours, from about 4 hours to about 8 hours, from about 8 hours to about 12 hours, from about 12 hours to about 15 hours, following the ischemic event. In some embodiments, an increased concentration of an ALDH1, ALDH3 and/or ALDH6 agonist is maintained in the plasma for at least several hours to several days following the radiation treatment.

For example, in some embodiments, a suitable ALDH agonist is administered to an individual with head and neck cancer within 1 minute to within 15 hours, e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 60 minutes to about 2 hours, from about 2 hours to about 4 hours, from about 4 hours to about 8 hours, from about 8 hours to about 12 hours, or from about 12 hours to about 15 hours, following radiation treatment.

As described above in the section entitled "Methods of Increasing Proliferation of Adult Salivary Stem Cells", the present disclosure provides methods that optionally include introducing an expanded population of adult salivary stem cells (e.g., where the expansion is effected by contacting the cells with an ALDH agonist, e.g., an activator of ALDH1 and/or ALDH3 and/or ALDH6) into a recipient individual. Introduction of the expanded salivary stem cells is useful in a variety of applications. For example, the introduced (e.g., "transplanted") salivary stem cells may engraft to an irradiated salivary gland and differentiate into functional saliva-producing cells, thereby restoring or enhancing the function of the irradiated salivary gland.

In certain aspects, the present disclosure provides treatment regimens that combine the post-radiation therapy introduction of an expanded population of adult salivary stem cells (e.g., as described above) with the pre- and/or post-radiotherapy administration (e.g., systemic and/or local administration) of an ALDH agonist to an individual (e.g., as also described above). As such, the present disclosure provides a treatment regimen wherein an individual with head and neck cancer receives an administration of an ALDH agonist (e.g., an activator of ALDH1 and/or ALDH3 and/or ALDH6) before radiotherapy, the treatment regimen further including introducing into the individual an expanded population of adult salivary stem cells as described above. The present disclosure further provides a treatment regimen wherein an individual with head and neck cancer receives an administration of an ALDH agonist (e.g., an activator of ALDH1 and/or ALDH3 and/or ALDH6) and an administration of an expanded population of adult salivary stem cells, with both administrations occurring after the radiotherapy. As will be appreciated, the present disclosure also provides a treatment regimen in which an ALDH agonist is administered systemically and/or locally to an individual before and after radiotherapy, the treatment regimen further including the introduction of an expanded population of adult salivary stem cells after the radiotherapy.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Adult Salivary Stem Cell Enrichment by Activation of Aldehyde Dehydrogenase 3 In Vivo In this study, human and murine submandibular gland (SMG) stem cells (SCs) were isolated and characterized, specifically with respect to the expression of different ALDH members in these cells compared to their non-stem cell (NSC) counterparts. It was found that adult human SMG SCs express different SC cell surface markers, including c-Kit, CD90, Nestin and CD44. Adult human SMG SCs also have higher levels of ALDH1 and ALDH3 isozymes than NSC. Functionally, adult human SMG SCs retain the ability to proliferate by forming BrdU$^+$ salispheres and to differentiate into different SMG lineages in culture. However, this cell population is rare; hence, there is a need to improve their yield. Treatment of adult mice with Alda89, an ALDH3 activator, resulted in more than doubling of c-Kit$^+$/CD90$^+$ SMG SC and BrdU$^+$ salisphere number. These data show that ALDH3 plays a role in SMG SC survival and that manipulating this pathway can be used for enrichment of these cells for use in therapy.

Materials and Methods
Human Salivary Tissue Collection

Salivary gland tissues were obtained from patients who underwent a neck dissection as part of their surgical treatment for HNC. All patients signed an informed consent approved by the Stanford Institutional Review Board (IRB).
Animal Studies All animal procedures were approved by the Institutional Animal Care and Use Committee at Stanford University. Female C57BL/6 mice (n=10, 4-5 weeks old, Jackson Laboratory, Sacramento, Calif.) were used for ALDH3 activator study.

Salivary Gland Tissue Dissociation

The isolation of human and mouse SMG tissues were performed as previously described by Szlavik V. et al. (Tissue Eng. Part A (2008) 14:1915-26). Salivary gland tissues were minced and dissociated in DMEM/F12 media (Gibco Invitrogen, Carlsbdad, Calif.) containing 0.1% trypsin-EDTA and 0.2 U/ml of liberase blendzyme 3 (Roche, Indianapolis, Ind.) for 4 hr at 37° C., centrifuges at 300×g and filtered through a Millipore filter (100 μm pore size, Millipore, Billerica Mass.). Primary cells were resuspended in DMEM/F12 medium supplemented with N2, B27, EGF (20 ng/ml), FGF2 (10 ng/ml) and IGF-1 (50 ng/ml), penicillin (100 U/ml)/streptomycin and (100 mg/ml), amphotericin-B (2.5 mg/ml) (Gibco Invitrogen, Carlsbdad, Calif.). The CD34 (human) and c-Kit (mouse) cells were isolated using the EASYSEP human CD34 and mouse c-Kit positive selection kit (STEMCELL Technologies Inc., Vancouver, BC).
Salispheres Formation and BrdU Analysis After 3 days of culture, cells were stained with Brdu staining kit according to the manufacturer's instructions (Invitrogen, Carlsbdad, Calif.). The total number of salispheres and BrdU positive salispheres per 96 well were counted under light microscopy. For each group 20 wells were counted and experiments were repeated 3 times.

The salispheres were also cultured in rat tail collagen 3D matrix (Roche, Indianapolis, Ind.). After 7 days of culture, the formation of ductal structures was examined. Images were captured with light microscopy under 400× magnification.
Immunohistochemistry Frozen tissue sections were warmed to room temperature and fixed on ice in acetone for 20 min. After fixation, slides were washed in phosphate buffered saline (PBS) solution. After overnight incubation at 4° C. with mouse anti-CD34 and mouse anti-c-Kit (1:100 dilution; BD Biosciences, San Jose, Calif.), the slides were rinsed with phosphate-buffered saline (PBS) and then incubated with either an Alexa Fluor 594 anti-mouse secondary antibody or Alexa Fluor 488 anti-mouse secondary (1:200 dilution; Invitrogen, Carlsbad, Calif.) at room temperature for 1 hour. The sections were then mounted with medium containing 4',6-diamidino-2-phenylindole (DAPI, Vector Laboratories, Burlingame, Calif.). Immunofluorescence images were acquired at 400× magnification using a Leica TCS SP2 confocal microscope (Leica Microsystems Inc., Bannockburn, Ill.).
FACS Analysis for Stem Cell Markers CD34 positive selected huSMG cells were incubated with anti-human CD34, CD90, c-Kit, CD44 and Nestin for 30 minutes on ice. The ALDEFLUOR kit was use to detect ALDH activity in the cells as an additional stem cell indicator (STEMCELL Technologies Inc., Vancouver, BC). The total cell viability was detected with a LIVE/DEAD fixable dead cell staining kit (Invitrogen, Carlsbad, Calif.) following manufacturer's suggested protocol. In addition, ArC amine reactive compensation beads (Invitrogen, Carlsbad, Calif.) were used as a positive staining control. The cells were analyzed using the LSR II analyzer (BD Biosciences) and FlowJo software (Tree Star, Asland Oreg.).
RNA Purification and Reverse Transcription Total RNA was extracted from CD34 (human) and c-Kit (mouse) positive and negative cells respectively using Trizol Reagent according to manufacturer's instruction (Invitrogen, Carlsbad, Calif.). Reverse transcription was performed on 500 ng of total RNA using random hexamer primer following manufacturer instruction (Applied Biosystems, Foster City, Calif.).

Quantitative Polymerase Chain Reaction (PCR)

Quantitative polymerase chain reaction (PCR) was performed on the cDNA samples using an Applied Biosystem 7900HT detection system (Applied Biosystems, Foster City, Calif.). The following primers were used: H18s sense primer CGGCTACCACATCCAAGGAA (SEQ ID NO:6), h18s anti-sense primer GCTGGAATTACCGCGGCT (SEQ ID NO:7), ALDH1A1 sense primer GCACGCCAGACTTACCTGTC (SEQ ID NO:8), ALDH1A1 anti-sense primer CCACTCACTGAATCATGCCA (SEQ ID NO:9), ALDH2A sense primer GAAACCATCCCCATTGACT (SEQ ID NO:10), ALDH2A anti-sense primer GTCTGCTCAGCTACCTTCATC (SEQ ID NO:11), ALDH1A3 sense primer ATCAACTGCTACAACGCCCT (SEQ ID NO:12), ALDH1A3 anti-sense primer TATTCGGCCAAAGCGTATTC (SEQ ID NO:13), ALDH3A2 sense primer CGCTCAACTCTTTCCCATTTG (SEQ ID NO:14), ALDH3A2 anti-sense primer TTCCCCAATCCACCTTTGAC (SEQ ID NO:15). Quantification of the samples was calculated from the threshold cycle by delta delta Ct method. The experiments were repeated four times on different patients' samples.

Primers for mouse ALDH1A3, ALDH2A, ALDH3A1, ALDH3A2 and ALDH6A are described in Levi, B. P. et al. (Blood (2009) 113:1670-80).

All PCR reactions were carried out in triplicate. DNA amplifications were carried out in a 384-well plate. The reactions were started for 2 min at 50° C., and then run at one cycle at 94° C. for 10 min and 45 of two-step repeats of 94° C. for 15 sec and 60° C. for 1 min. Fluorescence data were collected in real-time and analyzed with Sequence Detection System Software.

Treatment with ALDH3 Activator (Alda89)

An ALDH3 activator (Alda89, 100 ug/ml, n=5) and Vehicle control (50 µM; 50% DMSO and 50% PEG400, n=5) was injected into ALZET osmotic pumps (DURECT Corporation, Cupertino, Calif.). The osmotic pumps were implanted subcutaneously into C57BL/6 mice. The mice were euthanized after 7 days and salivary gland tissues were collected for analysis of salsiphere formation and BrdU incorporation as described above. In addition, FACs analysis for anti-mouse c-Kit and anti-mouse CD90 (BD Biosciences, San Jose, Calif.) cell population was also performed in pooled SMG samples.

Statistics

Data are expressed as mean±SEM. Statistical analysis of variance (ANOVA) and T-tests was use to compare the different number of salispheres, BrdU incorporation, and various ALDH isoform expressions in CD34/c-Kit positive cells from human and mouse salivary tissues. A p value 0.05 is considered to be significant.

Results

Isolation of Human Salivary Stem Cells

Figure 1B:
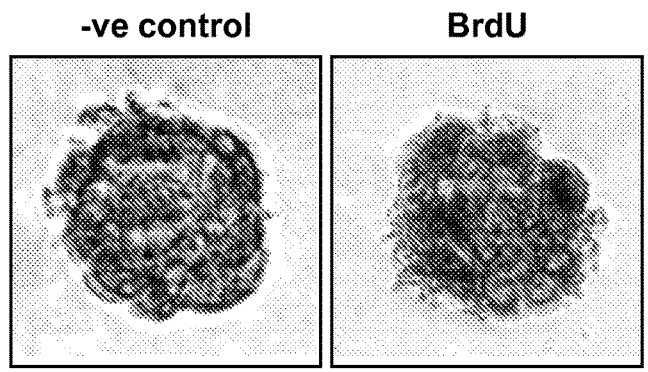
FIG. 1B shows the ability of CD34+ human salivary stem cells to form highly proliferative BrdU+ salispheres in culture.
Figure 1C:
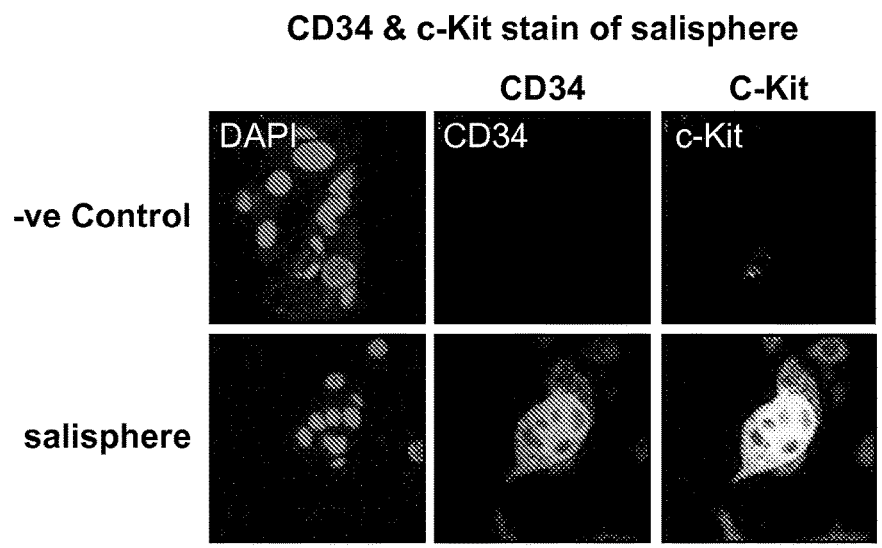
FIG. 1C shows that the salispheres retain positive staining for CD34 and c-Kit.
Figure 1D:
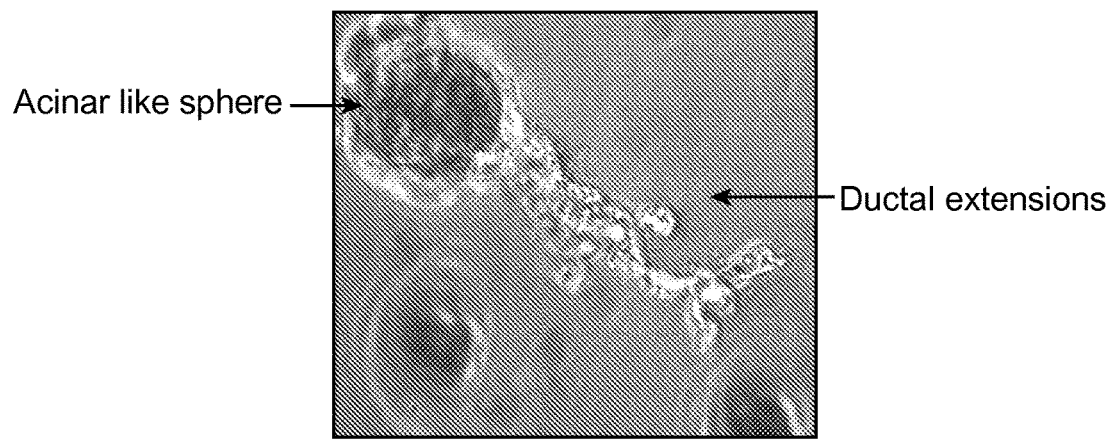
FIG. 1D shows that the salispheres are capable of forming acinar- and ductal-like structures.

Patient samples were dissociated and selected for $CD34^+$ cells. These cells were used for co-localization studies to characterize the presence of other SC surface markers by flow cytometry. As shown in FIG. 1A, >99% of viable $CD34^+$ cells also harbored c-Kit and CD90 on the cell surface and 70% were also positive for CD44 and Nestin. Functionally, these $CD34^+$ cells were able to form highly proliferative $BrdU^+$ salispheres in culture (FIG. 1B). The proliferative salispheres also retained positive staining for CD34 and c-Kit (FIG. 1C). When these spheres were placed in a 3D collagen matrix culture, they were able to form acinar- and ductal-like structures at day 7 (FIG. 1D). The overall SC yield by CD34 selection was estimated to be 0.3%. These results show that we have been able to isolate viable adult salivary SC from patients' SMG and these cells are quite rare in adult unirradiated glands.

ALDH3 Activation Increased $cKit^+/CD90^+$ Salivary Stem Cell Population

Figure 2A:
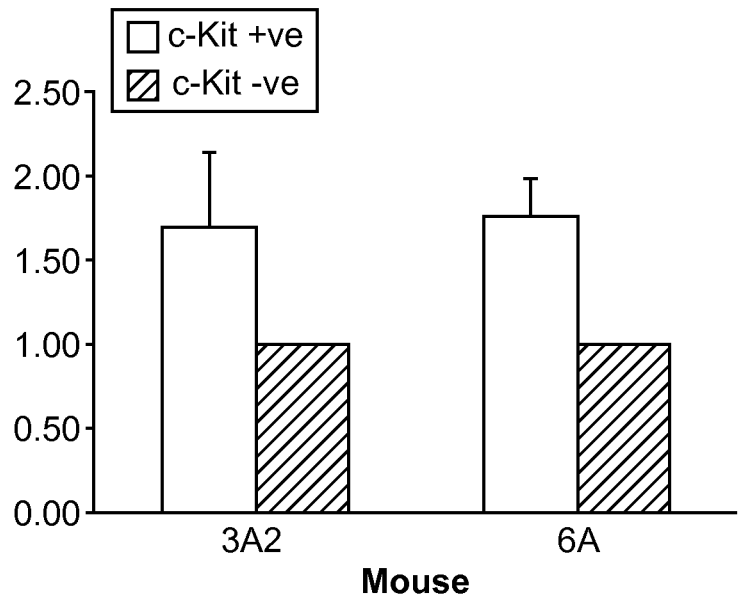
FIG. 2A and FIG. 2B show quantitative polymerase chain reaction results for ALDH expression in mouse c-Kit+ and human CD34+ submandibular gland cells, respectively.
Figure 2B:
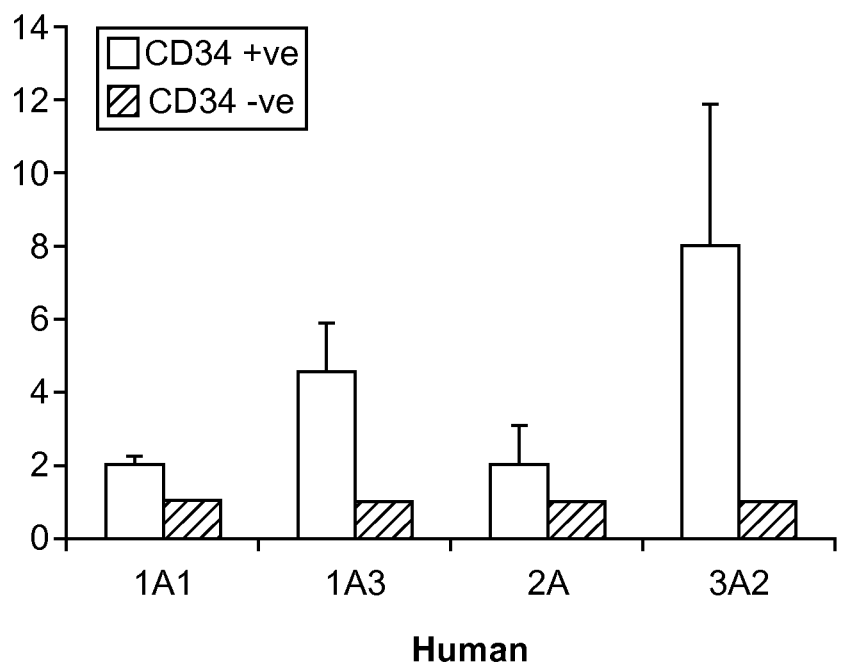

Quantitative PCR analysis of mouse SMG $c$-$Kit^+$ cells showed significantly higher levels of ALDH3A2 (1.70±0.44) and ALDH6A (1.76±0.22) expression when compared to c-Kit cells (FIG. 2A). The ALDH1A3 (1.04±0.02) and ALDH3A1 (1.10±0.05) expression levels in $c$-$Kit^+$ cells did not differ from the c-Kit cells. Additionally, ALDH2A (0.49±0.03) expression was significantly decreased in $c$-$Kit^+$ cells when compared to the negative control cells. Similarly, human SMG $CD34^+$ cells have higher expressions of ALDH3A2 (7.94±3.91) when normalized to the respective expressions in $CD34^-$ cells (FIG. 2B). Human SMG $CD34^+$ cells also had higher levels of ALDH1A1 (1.90±0.33) and ALDH1A3 (4.55±1.31) compared to NSC counterparts (FIG. 2B). The increased expression of ALDH2A (2.00±1.09) in the $CD34^+$ cells was not significant. Furthermore, analysis using the Aldefluor assay showed that 84% of the human SMG SC have high ALDH activity (FIG. 2C). Amplification of ALDH6 was incomplete in human cells.

Figure 3A:
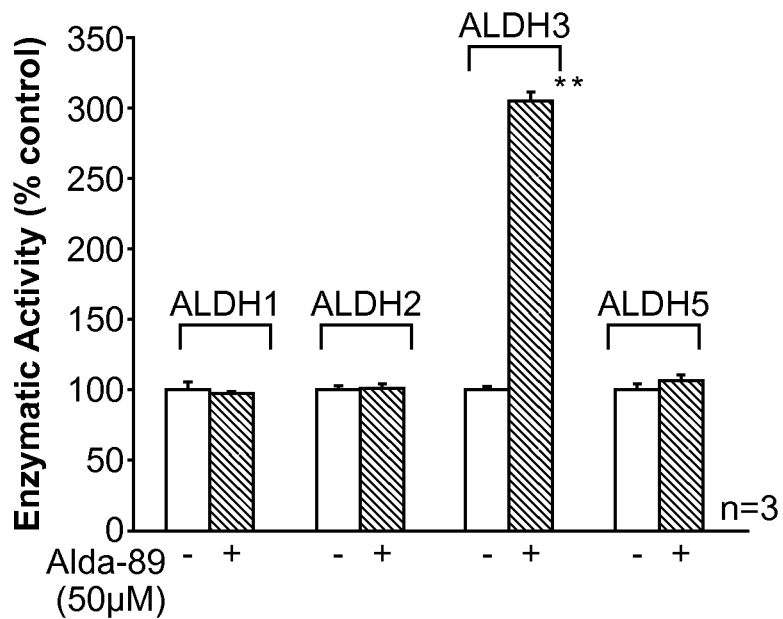
FIG. 3A shows isozyme selectivity of Alda-89 for ALDH3.
Figure 3B:
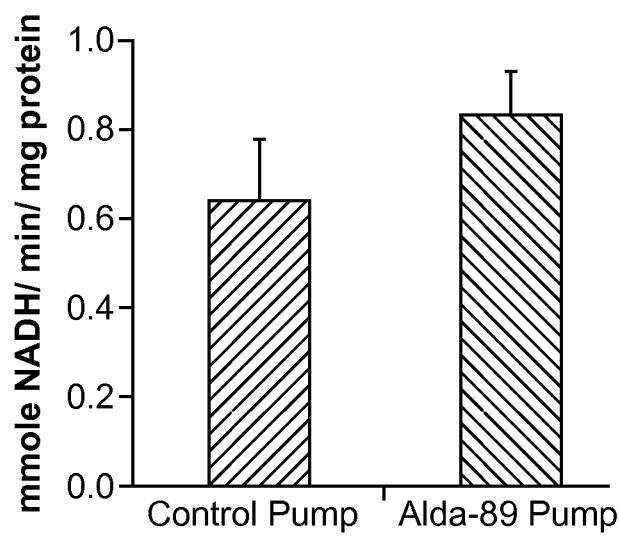
FIG. 3B shows the effect of Alda-89 infusion on ALDH3 expression in vivo.

Since the expression of the ALDH3A2 isoform was elevated in both human and murine SMG SC, the effect of activating this enzyme on salivary SC yield in mice was explored. An ALDH3 small molecular activator (Alda-89), which specifically activates ALDH3 enzymatically, was tested. Alda-89 is an ALDH3 isozyme-selective activator. Alda-89 significantly increases the catalytic activity of human ALDH3 recombinant enzyme by 304.4±7.1% of control (n=3, p<0.01), but has no effect on ALDH1, ALDH2 or ALDH5 isozyme (FIG. 3A). In vivo, infusion of Alda89 into mice by an osmotic infusion pump at 34 mg/kg/day successfully enhanced ALDH3 enzyme activity by 29% in esophagus cell homogenate as compared to vehicle control (n=5, p<0.05) (FIG. 3B).

Figure 3C:
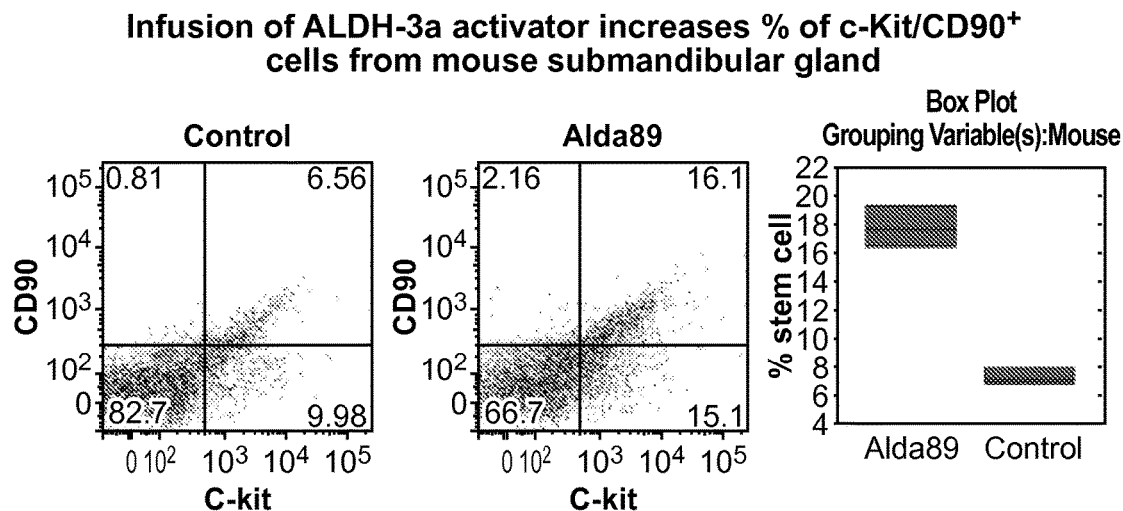
FIG. 3C shows the effect of Alda-89 infusion in mice on the number of c-Kit+/CD90+ submandibular gland cells.
Figure 3D:
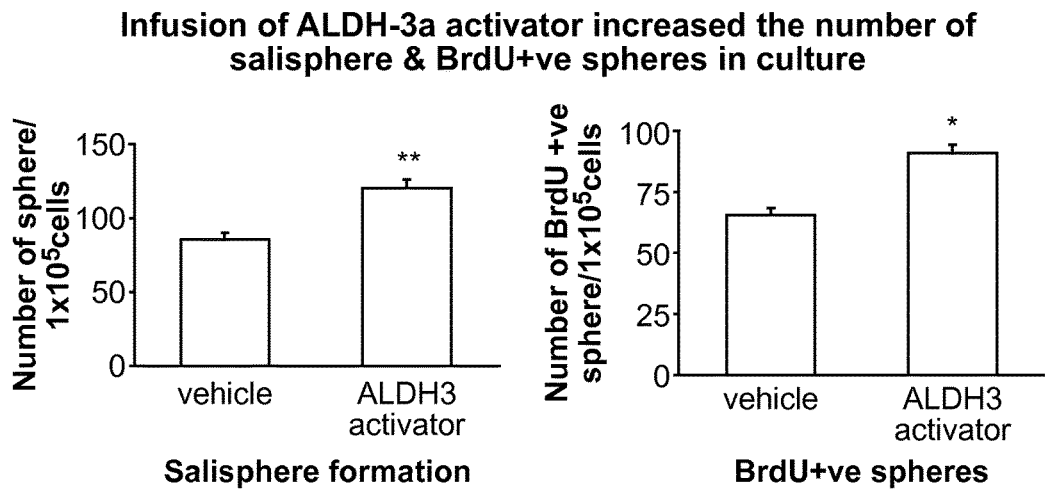
FIG. 3D shows the effect of Alda-89 infusion on the number of salispheres and BrdU-positive spheres.

Mouse SMGs were collected after 7 days of Alda89 treatment and assayed for the number of $c$-$kit^+/CD90^+$ cells. As shown in FIG. 3C, Alda89 treatment more than doubled the number of $c$-$kit^+/CD90^+$ cells when compared to the vehicle control (17.8±0.95% vs. 7.37±0.45%, p<0.05). In addition, unselected SMG cells were collected and cultured to examine the effects of Alda89 on $BrdU^+$ salisphere formation. Parallel to the increase in $c$-$kit^+/CD90^+$ cells, the total number of salispheres were significantly greater in the Alda89 treated group compared to vehicle control (121±0.83 spheres/5000 cells vs. 86±0.58 p<0.05, FIG. 3D, left). Additionally, the number of $BrdU^+$ spheres were also significantly higher in the Alda89 treated group (91±0.83 spheres/5000 cells vs. 66±1.42, p<0.05, FIG. 9D, right). These data indicated that pharmacologic activation of ALDH3 was sufficient to enhance adult SMG SC yield.

In addition, it was investigated whether human salivary cells can be implanted into the submandibular gland of an irradiated nude mouse. As shown in FIG. 4, HLA-ABC staining of human cells implanted into the SMG of a recipient irradiated nude mouse indicates successful implantation of the human cells.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope

What is claimed is:

1. A method of increasing proliferation of adult salivary stem cells in an individual having a head and neck cancer and suffering from, or being at risk of suffering from, radiotherapy-related xerostomia, the method comprising:
selectively increasing an enzymatic activity of ALDH-3 in adult salivary stem cells in vivo, by administering a therapeutically effective amount of a selective ALDH-3 agonist continuously from 1 week preceding radiation treatment and at least 3 weeks after radiation treatment, wherein said method increases the number of adult salivary stem cells in the individual having the head and neck cancer and suffering from, or being at risk of suffering from, radiotherapy-related xerostomia by at least 25%, and the ALDH3 agonist is a compound having a structure:

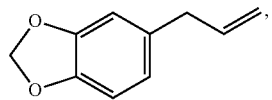
(Alda-89)

or a pharmaceutically acceptable salt thereof.

2. A method of treating an individual having a head and neck cancer and suffering from, or being at risk of suffering from, radiotherapy-related xerostomia, the method comprising:

a) continuous administration of a therapeutically effective amount of Alda-89 up to 1 week before subjecting the individual to radiation therapy;
b) subjecting the individual to radiation therapy; and
c) selectively increasing an enzymatic activity of ALDH-3 in adult salivary stem cells in the individual by continuous administration of a therapeutically effective amount of Alda-89 at least three weeks after radiation therapy, wherein said method increases the number of functioning saliva-producing cells in the individual.

3. The method of claim 2, wherein the administering comprises orally administering, intravenously administering, locally injecting, or topically applying the Alda-89 to the individual.

4. The method of claim 2, Alda-89 is formulated in a pharmaceutical composition comprising the ALDH-3 agonist and a pharmaceutically acceptable excipient.

5. The method of claim 2, wherein the Alda-89 is administered via an osmotic pump.

6. The method of claim 2, wherein the Alda-89 is administered in an amount of from 25 mg/kg/d to 50 mg/kg/d for the duration of treatment.

7. The method of claim 2, wherein the Alda-89 is administered in an amount of from 50 mg/kg/d to 100 mg/kg/d for the duration of treatment.

8. The method of claim 7, wherein the Alda-89 is administered for a duration of from one month to 3 months.

* * * * *